United States Patent
Shimizu et al.

(10) Patent No.: US 8,897,864 B2
(45) Date of Patent: Nov. 25, 2014

(54) HEART RATE METER AND METHOD FOR REMOVING NOISE OF HEART BEAT WAVEFORM

(75) Inventors: Hideki Shimizu, Saitama (JP); Tsuneharu Kasai, Saitama (JP)

(73) Assignee: Citizen Holdings Co., Ltd., Tokyo (JP)

( * ) Notice: Subject to any disclaimer, the term of this patent is extended or adjusted under 35 U.S.C. 154(b) by 1613 days.

(21) Appl. No.: 12/066,943

(22) PCT Filed: Sep. 5, 2006

(86) PCT No.: PCT/JP2006/317523
§ 371 (c)(1),
(2), (4) Date: Mar. 14, 2008

(87) PCT Pub. No.: WO2007/032226
PCT Pub. Date: Mar. 22, 2007

(65) Prior Publication Data
US 2009/0112111 A1   Apr. 30, 2009

(30) Foreign Application Priority Data
Sep. 15, 2005 (JP) ................................ 2005-268717

(51) Int. Cl.
*A61B 5/0402* (2006.01)
*A61B 5/024* (2006.01)
*A61B 5/00* (2006.01)

(52) U.S. Cl.
CPC .............. *A61B 5/024* (2013.01); *A61B 5/02416* (2013.01); *A61B 5/7207* (2013.01); *A61B 5/02405* (2013.01)
USPC ........................................................ 600/519

(58) Field of Classification Search
USPC .......... 600/509, 513, 515, 516, 520; 607/7, 9, 607/14, 17
See application file for complete search history.

(56) References Cited

U.S. PATENT DOCUMENTS 5,503,159 A * 4/1996 Burton .......................... 600/516
5,993,401 A   11/1999 Inbe et al.
(Continued)

FOREIGN PATENT DOCUMENTS

JP         61-29730 B2    7/1986
JP         4-79250 B2    12/1992
(Continued)

OTHER PUBLICATIONS

International Search Report of PCT/JP2006/317523, date of mailing Oct. 3, 2006.
(Continued)

*Primary Examiner* — Kennedy Schaetzle
*Assistant Examiner* — Erica Lee
(74) *Attorney, Agent, or Firm* — Westerman, Hattori, Daniels & Adrian, LLP

(57) ABSTRACT

A heart rate meter for measuring the heart rate of a living body includes a heart rate variation detecting unit for measuring the variation of the heart rate determined from a heart beat waveform, and a heart rate error detecting and correcting unit for detecting an error of heart rate on the basis of the trend of the heart rate variation and correcting the heart rate error being detected. The heart rate error detecting and correcting unit includes a heart rate error detecting unit for detecting an error of the heart rate variation as a heart rate error on the basis of the trend of the heart rate variation, and a heart rate error correcting unit for correcting the error of heart rate according to the detection of the heart rate error.

13 Claims, 23 Drawing Sheets

(56) References Cited

U.S. PATENT DOCUMENTS

| | | | |
|---|---|---|---|
| 7,139,604 B1 * | 11/2006 | Mouchawar et al. | 600/509 |
| 7,381,185 B2 * | 6/2008 | Zhirnov et al. | 600/300 |
| 2002/0065473 A1 * | 5/2002 | Wang et al. | 600/518 |
| 2002/0120306 A1 * | 8/2002 | Zhu et al. | 607/25 |
| 2002/0165586 A1 * | 11/2002 | Hill et al. | 607/9 |

FOREIGN PATENT DOCUMENTS

| | | |
|---|---|---|
| JP | 9-173306 A | 7/1997 |
| JP | 11-9564 A | 1/1999 |
| JP | 2001-198094 A | 7/2001 |
| JP | 2003-310562 A | 11/2003 |

OTHER PUBLICATIONS

Notification of Transmittal of Translation of the International Preliminary Report on Patentability (Form PCT/IB/338) of International Application No. PCT/JP2006/317523 mailed Mar. 27, 2008 with Forms PCT/IB/373, PCT/IB/326, PCT/ISA/237 and English translation.

* cited by examiner

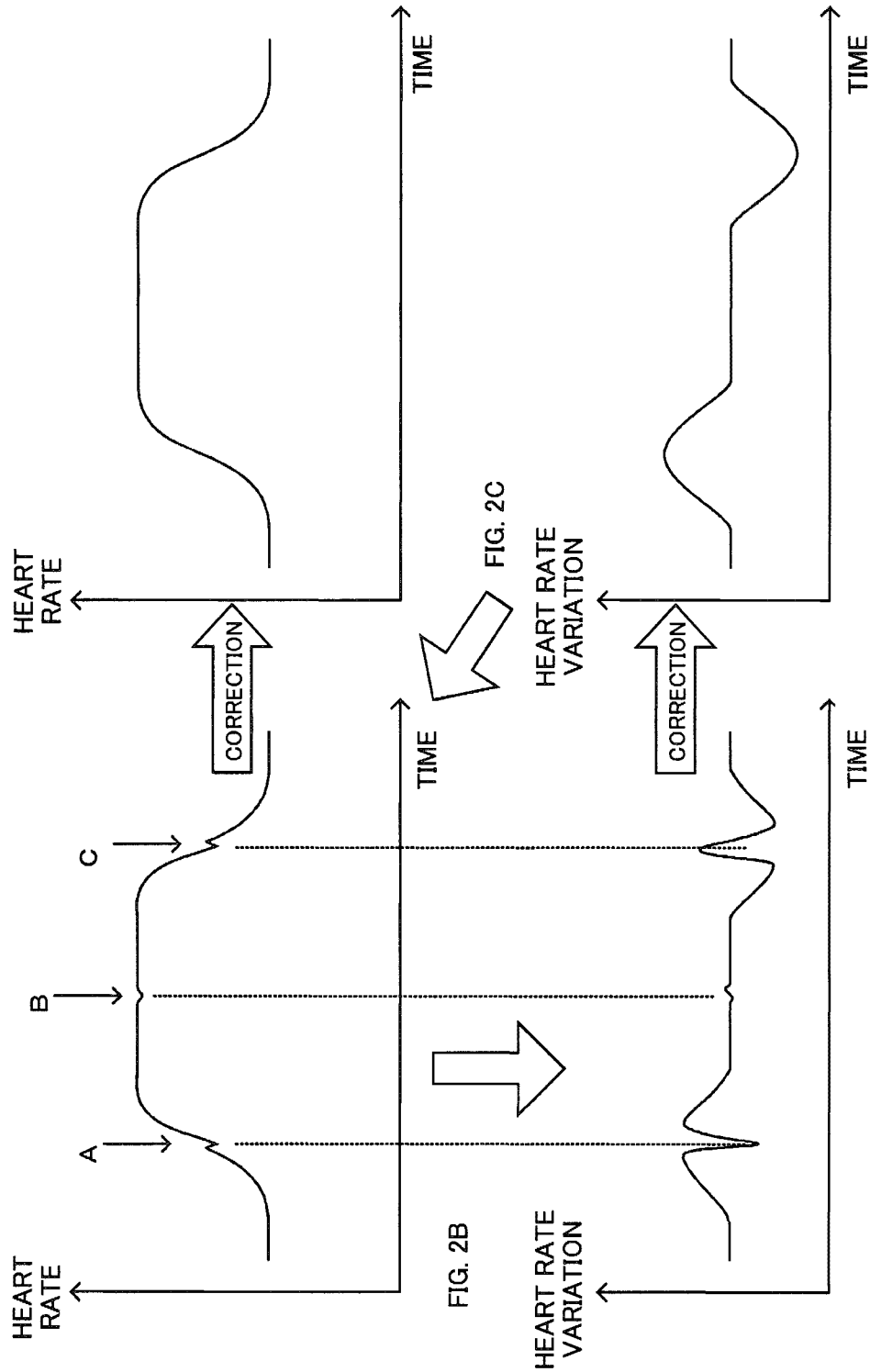

CORRECT HEART
RATE VARIATION

ERRONEOUS HEART
RATE VARIATION

REFERENCE HEART
RATE VARIATION
PATTERN

COMPARISON OF
HEART RATE
VARIATION PATTERNS

SELECT

CORRECTED HEART
RATE VARIATION

HEART RATE

HEART RATE VARIATION

CORRECTED HEART RATE

CORRECTED HEART RATE VARIATION

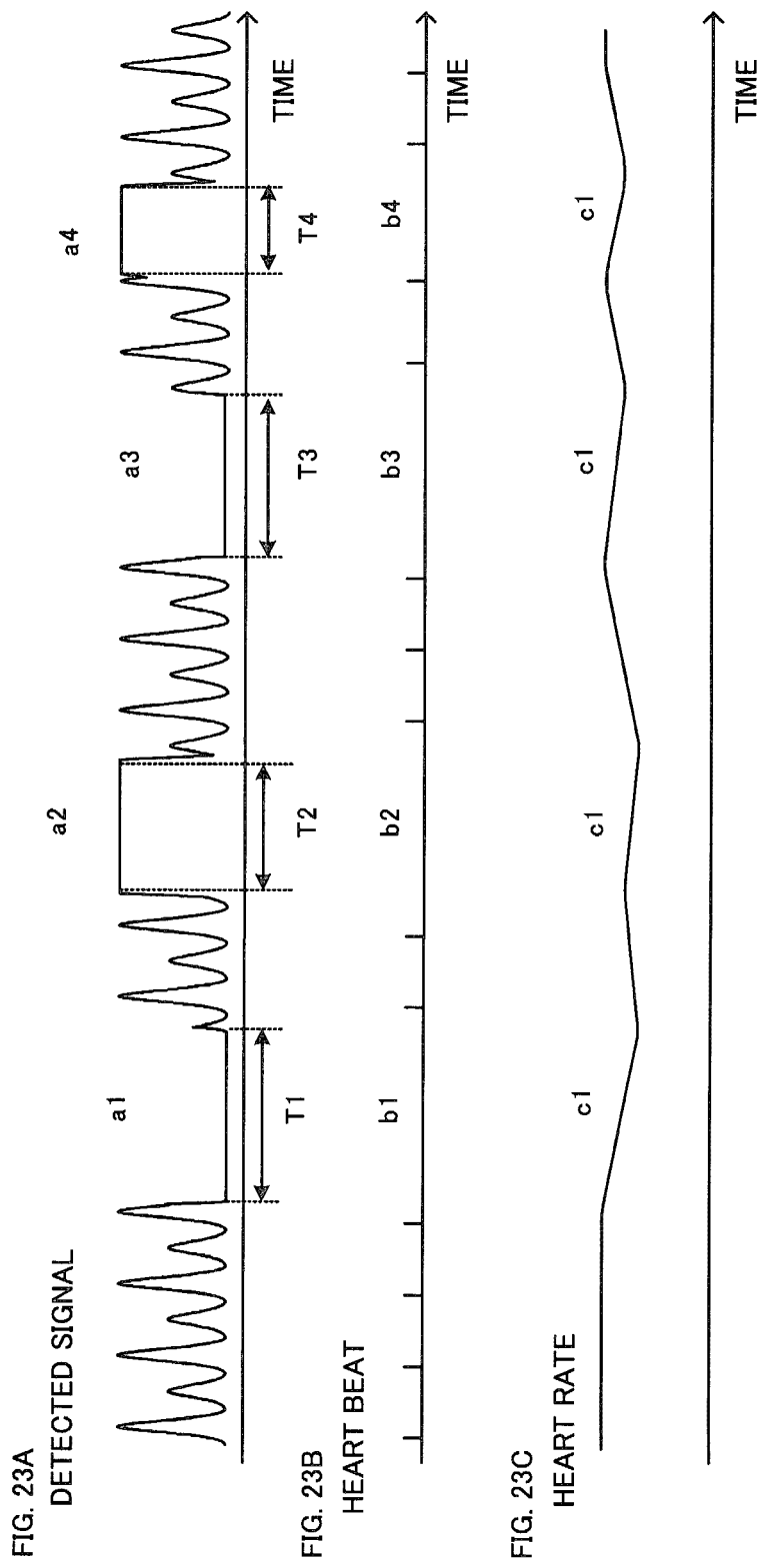

HEART RATE METER AND METHOD FOR REMOVING NOISE OF HEART BEAT WAVEFORM

TECHNICAL FIELD

The present invention relates to a heart rate meter and a method for removing noise of heart beat waveform, and more particularly, it relates to a method for removing noise caused by a body motion.

BACKGROUND ART

Conventionally, various heart rate meters have been suggested for measuring heart rate of a living body. By way of example, patent document 1 is known as disclosing a pulse detecting circuit which irradiates a light from a light emitting device onto a body, detects a reflected light or a transmitted light therefrom by a light receiving device, and converts a received signal into a pulse signal, thereby detecting the pulse.

With the heart rate meter as described above, it is demanded that the pulse rate is stably displayed as against a noise, and there are some suggestions for enhancing the stability of the pulse rate display (e.g., patent document 2, patent document 3, and patent document 4).

The patent document 2 discloses a technique which focuses attention on the point that a pulse width caused by a noise is relatively narrow, and provides a pulse wave evaluation means between a pulse wave detecting circuit and a pulse wave operation means for evaluating the pulse width of pulse signals outputted from the pulse wave detecting circuit. With the pulse wave evaluation means, only a signal evaluated as a normal pulse wave signal is transferred to the pulse wave operation means, and thereby obtaining a stability in displaying the pulse.

The patent document 3 discloses a technique to remove a body motion by using an acceleration sensor and wavelet transformation. In this document, it is disclosed as the following: the acceleration sensor detects a body motion waveform assuming the body motion as an acceleration, and the body motion waveform is subjected to the wavelet transformation to generate body motion analytical data for each frequency domain; in addition, a pulse waveform detected from a detection target part of the living body is subjected to the wavelet transformation to generate pulse wave analytical data for each frequency domain; and the body motion analytical data is subtracted from the pulse wave analytical data, so as to detect a pulse.

The patent document 4 also discloses that in the photoplethysmography (PPG) for optically detecting heart rate information, a noise being a high frequency component, is removed from a PPG signal by using the wavelet transformation.

Patent document 1: Japanese Examined Patent Application Publication No. 61-29730
Patent document 2: Japanese Examined Patent Application Publication No. 04-79250
Patent document 3: Japanese Unexamined Patent Application Publication No. 11-9564
Patent document 4: Japanese Examined Patent Application Publication No. 2003-310562

DISCLOSURE OF THE INVENTION

Problems to be Solved by the Invention

A heart rate is measured by a heart rate meter under various measuring conditions, such as during non-exercise and during exercise. Heart beat waveforms detected by the heart rate meter under such various conditions may have not only basic waveforms but also noise components superimposed thereon, which are different in signal properties such as frequency and crest value.

During exercise, in addition to the basic wave and higher harmonic wave, which constitute primary components, a noise component is superimposed on the heart beat waveform. This noise component may include a disturbance noise being an electrical high frequency noise, which breaks into the heart rate sensor and a transmission system, and further includes a motion artifact being a micro vibration generated due to a positional displacement of a mounting point of the heart rate sensor, which occurs when a person to be measured with the heart rate sensor mounted thereon performs exercise.

Furthermore, the motion artifact is roughly classified into two types, according to a generating factor and an error size of the noise.

One type is the noise that may occur in the case where a position of the heart rate sensor is displaced even being held on a blood vessel, and thereby a micro vibration is superimposed on the heart beat waveform level. In this case, a heart rate error being around less than 20 beats/60 seconds may be observed in most situations. The other type is the noise that may occur in the case where the heart rate sensor comes off the blood vessel, and therefore any heart beat waveforms are not outputted at all, or abnormal oscillation occurs due to a disturbance light. In this case, a heart rate error of not less than 20 beats/60 seconds may be observed in most situations.

With regard to the motion artifact as described above, if the heart rate sensor comes off the blood vessel as in the latter case, and any heart beat waveforms are not outputted at all, or abnormal oscillation occurs due to the disturbance light, the heart rate is not counted in any of these cases.

FIGS. 23A-C show illustrations for explaining a heart rate error due to a motion artifact that is generated when the heart rate sensor is moved considerably.

FIG. 23A shows a heart beat waveform outputted from the heart rate sensor. In the periods of a1 and a3, the heart beat waveform is not outputted at all, and in the periods of a2 and a4, the output is saturated by the abnormal oscillation. In the periods of a1 to a4, respectively in time zones of T1 to T4, it is not possible to detect a heart rate from the heart beat waveform (b1 to b4 in FIG. 23B).

Since the heart rate is expressed by the heart beats per unit time, the heart rate is turned down in each of the period c1 to the period c4 as shown in FIG. 23C.

A disturbance noise being an electrical high frequency noise that breaks into the heart rate sensor and transmission system, and a motion artifact which is generated by a positional displacement of a mounting point of the heart rate sensor have a form that noise components are superposed on major components of the heart beats. Therefore, a method of noise removal by the use of signal processing, such as filtering, is applicable.

However, in the case where the heart rate sensor comes off the blood vessel position and the heart beat waveform is lost or oscillated as described above, the major components of the heart beats are lost. Therefore, it is not possible to apply the method of the noise removal according to the signal processing, which is disclosed in the aforementioned patent documents.

As described above, if a considerable motion artifact occurs, there is a problem that an accurate heart rate is hardly acquired by the method which subjects the heart beat waveform as an output from the heart rate sensor to the signal processing.

In view of the situation above, an object of the present invention is to solve the conventional problem and to acquire an accurate heart rate even when the major components of the heart beats are lost due to a considerable motion artifact or the like.

Means to Solve the Problems

The present invention is directed to a heart rate meter for measuring a heart rate of a living body, including, a heart rate variation detecting unit for obtaining a heart rate variation determined from a heart beat waveform, and a heart rate error detecting and correcting unit for detecting a heart rate error based on a trend of the heart rate variation and correcting the heart rate error being detected.

The present invention is further directed to a method for removing a noise in a heart beat waveform, including, a heart rate variation detecting step for obtaining a heart rate variation determined from a heart beat waveform, and a heart rate error detecting and correcting step for detecting a heart rate error based on a trend of the heart rate variation and correcting the heart rate error being detected.

In order to express the heart rate, for example, a heart rate sensor detects heart beats from a living body, subjects the heart beat waveform being outputted to a signal processing to extract each of the heart beats, counts the heart beats, and then converts the heart beats into the number of heart beats per unit time (e.g., 1 minute).

Here, the heart rate variation represents how the heart rate described above changes in time wise. The heart rate variation can be expressed by the variation in the number of heart beats in a predetermined period of time, increased or decreased. For example, if the heart rate in a predetermined period of time is changed from 80 beats/min to 100 beats/min, in the period before and in the period after, it means that the heart rate is increased by 20 beats as the difference therebetween, and the heart rate variation is "+20 beats". The predetermined period of time may be any length as far as it is longer than the heart beat interval. For example, 30 seconds may be set as a unit.

In addition to the variation in the number of heart beats as described above, the heart rate variation may also be expressed by a differential value of the heart rate at a predetermined point of time. The heart rate is obtained by counting the heart beats of a living body, inherently being discontinuous quantity, and therefore a differential value cannot be obtained as to the heart rate itself. However, a temporal change of the heart rate is approximated by a function and thereby obtaining the differential value of the heart rate.

In measuring the heart beat, if information as to the heart beat is lost due to a considerable motion artifact, or the like, it is not possible to detect from the heart beat waveform itself, major components, heart beat position, and the like, for specifying the heart beat.

In view of the situation above, the heart rate meter and the method for removing a noise of heart beat waveform, according to the present invention, obtain the heart rate variation as to the heart rate obtained from the heart beat waveform, detect an error in the heart rate based on a trend of the heart rate variation, and correct the heart rate in which an error is detected. Accordingly, even when major components of heart beats are lost due to a considerable motion artifact, or the like, an accurate heart rate can be acquired.

According to more than one aspects of the present invention, the heart rate variation can be detected.

In a first aspect of the invention for detecting the heart rate variation, the heart rate variation is obtained from the variation in the heart rate every predetermined period of time.

Then, it is possible to obtain the variation in the heart rate from a difference in sampling values of the heart rate, for instance.

In a second aspect of the invention for detecting the heart rate variation, a heart rate variation is obtained from a differential value of the heart rate at a predetermined point of time.

Inventors in the present patent application have found that as to the heart rate, there are differences among individuals, depending on the persons being measured, but as to the heart rate variation, there is a common trend in variation even when different persons are measured. In particular, it is found that the heart rate variation, which appears when a certain level of load is applied on the person to be measured, shows a common characteristic variation trend.

FIG. 1A illustrates the heart rate and FIG. 1B illustrates heart rate variation when a certain level of load is applied. Here, the heart rate variation is expressed by the variation in the heart rate every predetermined period of time.

There are various sizes of the heart rate depending on differences among individuals, as to the persons being measured, but the heart rate variation shows a trend in variation that is substantially common within a predetermined variation range. For example, the heart rate variation has a trend that when an exercise is started, the heart rate is once increased, and thereafter, it starts decreasing. After the increase and decrease of the heart rate variation, the heart rate is maintained virtually constant during the exercise. On the other hand, when the exercise is finished, the heart rate variation shows a trend in such a manner that the heart rate is once decreased, and thereafter, it starts increasing. According to the heart rate variation, after the end of the exercise, the heart rate resumes to the state before the exercise, after lapse of a predetermined period of time.

This heart rate variation shows a variation trend substantially common within a predetermined variation range, regardless of individual differences among the persons to be measured.

The present invention focuses attention on this heart rate variation. Due to a considerable motion artifact, or the like, a loss of detected signals of the heart beat waveform (a1 and a3 in FIG. 23A) and a saturation caused by the oscillation of detected signals of the heart beat waveform (a2 and a4 in FIG. 23A) occur. Errors in the heart rate caused by those factors are detected from errors in the heart rate variation. Next, the detected error part in the heart rate variation is corrected by a reference heart rate variation, and further the heart rate is corrected based on the heart rate variation being corrected.

The heart rate error detection and correction includes a heart rate error detection that detects a heart rate variation error based on the trend of the heart rate variation, so as to obtain a heart rate error, and a heart rate error correction that corrects the heart rate error according to the detection of the heart rate error.

FIGS. 2A-2D illustrate detection of a heart rate variation error, correction of the heart rate variation error, which are performed on the basis of the heart rate variation, and correction of an error in the heart rate. When loss of the heart beat information occurs due to motion artifact, at some parts of the heart rate (A, B, and C in the figure) (FIG. 2A), errors occur in the heart rate variation due to such loss of the heart rate information (FIG. 2B). These errors in the heart rate variation are detected, and then they are corrected (FIG. 2C). The heart rate variation is corrected, and thereby the heart rate variation being corrected is made to include information that relates to the heart rate being corrected.

According to the heart rate variation being corrected (FIG. 2C), the heart rate including the error (FIG. 2A) is corrected, and a corrected heart rate is obtained (FIG. 2D).

In the present invention, the heart rate error detection includes, a heart rate variation error detection for comparing a trend of the heart rate variation of a target heart rate with a trend of a reference heart rate variation as a standard, and detecting an error in the target heart rate variation based on a trend similarity between both of the heart rate variations, and a heart rate variation error correction for correcting the heart rate variation error.

In the heart rate variation error detection, multiple number of heart rate variation values included in the target heart rate variation within a predetermined time zone are assumed as the trend of the heart rate variation, the heart rate variation values of the same number held in the reference heart rate variation within the same predetermined time zone are assumed as the trend of the reference heart rate variation, and differences between the heart rate variation values associated respectively in both trends, are assumed as the trend similarity. Then, an error in the target heart rate variation is detected.

The heart rate variation error detection process can be performed as the following; multiple reference heart rate variation patterns are prepared, each being made up of a different combination of heart rate variation values, and the reference heart rate variation pattern estimated from the multiple reference heart rate variation patterns is compared with the target heart rate variation.

The timing when the reference heart rate variation pattern used for the comparison is estimated from the multiple reference heart rate variation patterns can be set in sync with the timing when an exercise load is applied.

In the heart rate variation error detection, an error in the heart rate variation is detected based on the number of the target heart rate variation values each having a difference which goes over a set value. For example, if at least one value among the multiple heart rate variation values constituting the heart rate variation pattern is out of the range of the heart rate variation value of the reference heart rate variation pattern, it is determined that there is an error in the heart rate variation.

When an error is detected, according to the heart rate variation error correction, the heart rate variation value of the target heart rate variation detected in the heart rate variation error detection is corrected to the heart rate variation value of the reference heart rate variation.

Furthermore, a heart rate error correcting unit corrects an associated heart rate, according to the heart rate variation value being detected and corrected in the heart rate variation error detection.

Effect of the Invention

According to the present invention, even when major components of the heart beat are lost due to a considerable motion artifact, or the like, it is possible to acquire an accurate heart rate.

BRIEF DESCRIPTION OF THE DRAWINGS

FIGS. 2A, B, C and D illustrate detection of heart rate variation errors according to the heart rate variation, correction of the heart rate variation errors, and correction of heart rate errors;

FIGS. 23A, B and C show illustrations for explaining errors in heart beats due to a motion artifact that is generated when the heart rate sensor is moved considerably.

DESCRIPTION OF THE MARKS

1 HEART RATE METER
2 HEART RATE SENSOR
2a LIGHT EMITTING DEVICE
2b LIGHT RECEIVING DEVICE
2c LIGHT SHIELDING
2A TACTILE SENSOR
3 DETECTING CIRCUIT
4 HEART RATE DETECTING UNIT
5 HEART RATE VARIATION DETECTING UNIT
5a HEART RATE TEMPORARY STORAGE
5b DIFFERENCE OPERATION PART
5c HEART RATE VARIATION STORAGE
6 HEART RATE ERROR DETECTING AND CORRECTING UNIT
6A HEART RATE ERROR DETECTING UNIT
6B HEART RATE ERROR CORRECTING UNIT
6a HEART RATE VARIATION ERROR DETECTING PART

6b REFERENCE HEART RATE VARIATION PATTERN STORAGE
6c REFERENCE HEART RATE VARIATION PATTERN SELECTING PART
6d HEART RATE VARIATION CORRECTING PART
6e HEART RATE STORAGE
6f CORRECTED HEART RATE OPERATION PART
6g REWRITING PART
7 HEART RATE COUNTER
8 HEART RATE NOTIFICATION UNIT
9 LIGHT EMITTING CIRCUIT
10 SIGNAL PROCESSOR
21 DELAY UNIT
22 ADDER
23 COMPARATOR
24 ADDER
25 COMPARATOR
30 LIVING BODY
31 BLOOD VESSEL
32 OSCILLATING WAVE
33 BODY TISSUE
34 SKIN

BEST MODE FOR CARRYING OUT THE INVENTION

Hereinafter, a heart rate meter and a procedure for detecting a heart rate by removing noise components from a heart beat waveform according to the present invention will be explained in detail, with reference to the accompanying drawings.

Figure 1A:
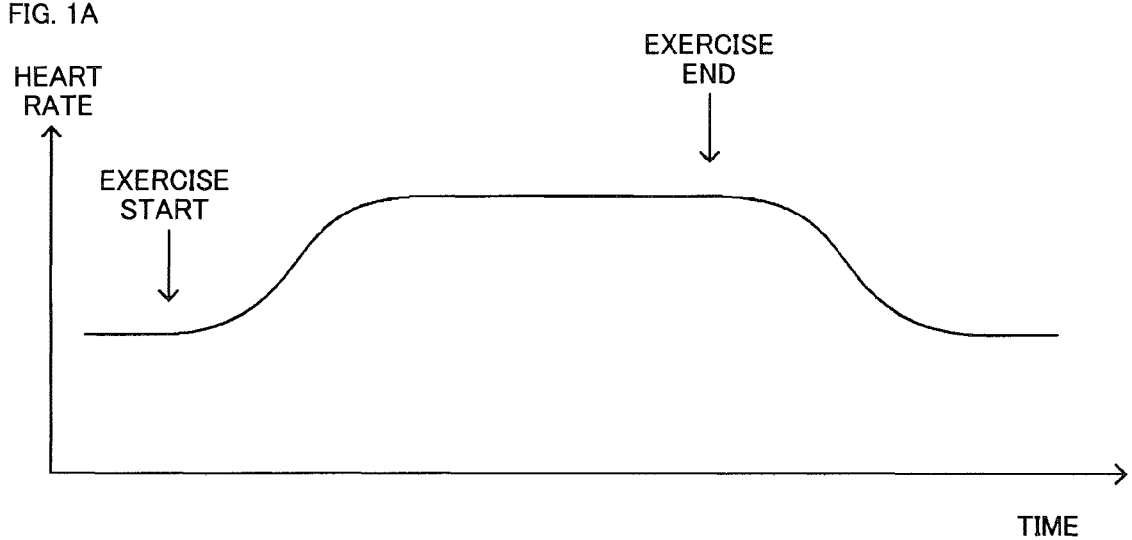
FIG. 1A illustrates the heart rate and FIG. 1B illustrates the heart rate variation when a load of a certain level is applied.
Figure 1B:
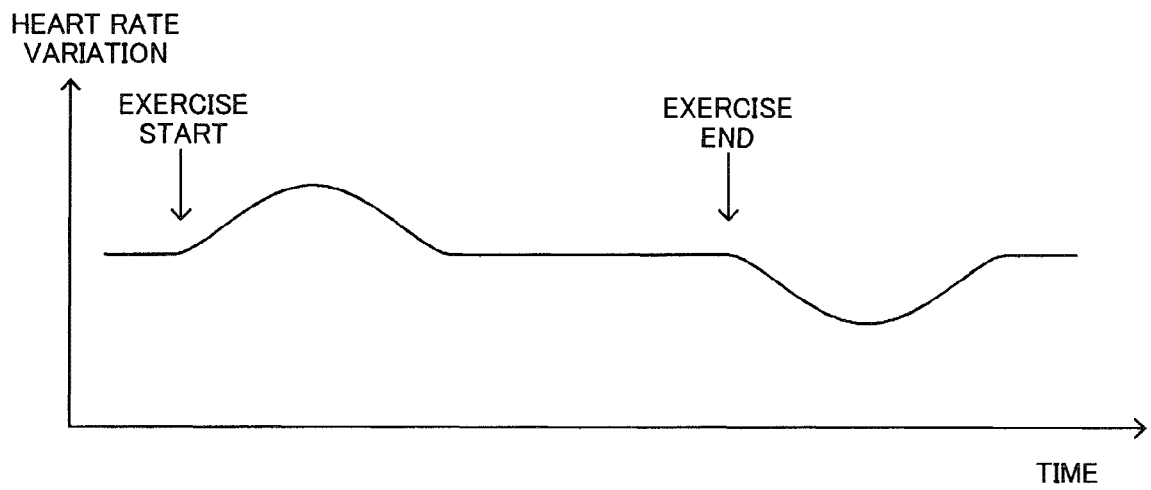
Figure 3:
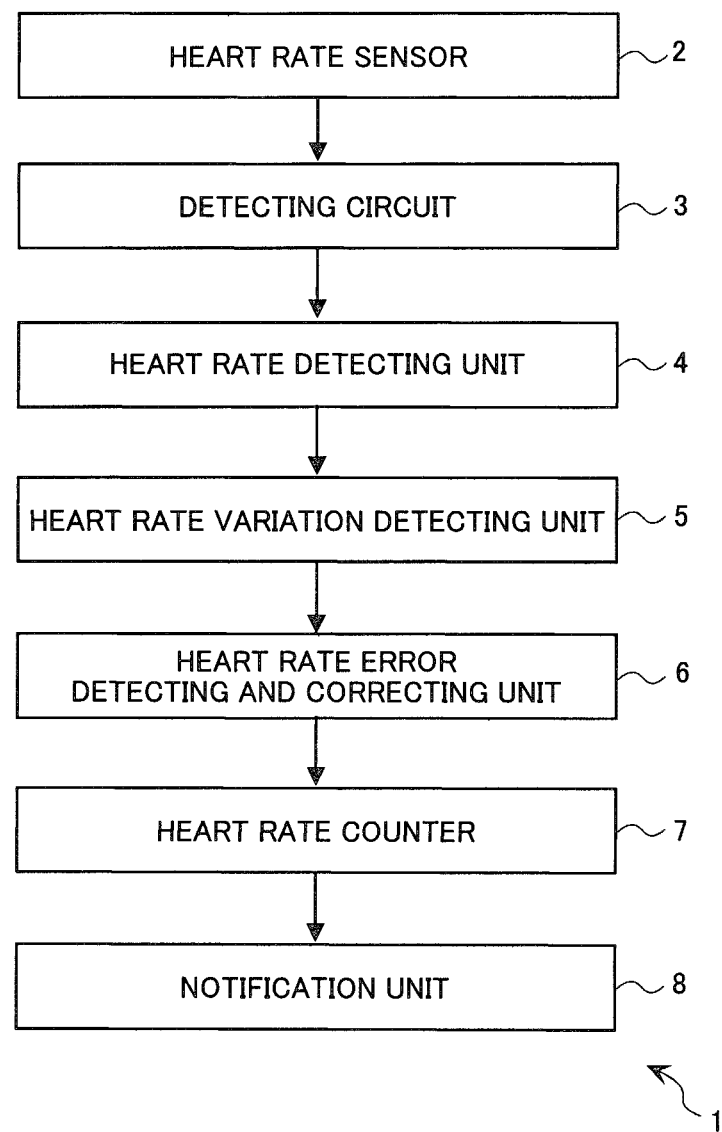
FIG. 3 is a diagram for explaining a schematic configuration of the present invention.

Firstly, a schematic configuration of the present invention will be explained with reference to FIG. 3. In FIG. 3, a heart rate meter 1 of the present invention includes a heart rate detecting unit for detecting a heart beat waveform of a living body, and a signal processor for detecting the heart rate that is obtained by subjecting the detected heart beat waveform to a signal processing. A heart rate counter 7 counts the heart rate detected in the signal processor, and a heart rate notification unit 8A (not illustrated) provided in a notification unit 8 notifies the counted heart rate, by means of display, transmission, recording, and the like.

It is to be noted here that the heart rate detecting unit may be made up of a heart rate sensor 2, and a detecting circuit 3 which acquires a detected signal from the output of the heart rate sensor 2, for instance. By way of example, an optical sensor may serve as the heart rate sensor 2, and the detecting circuit 3 converts the output such as an optical signal, acquired from the heart rate sensor 2 into an electrical signal. If necessary, the detecting circuit 3 subjects the signal to amplification, and converts the signal into a digital signal according to A/D conversion.

The signal processor includes a heart rate detecting unit 4 for detecting a heart rate based on the heart beat waveform detected in the detecting circuit 3, a heart rate variation detecting unit 5 for detecting a heart rate variation based on the heart rate detected in the heart rate detecting unit 4, and a heart rate error detecting and correcting unit 6 for detecting a heart rate error based on the heart rate variation detected in the heart rate variation detecting unit 5, and corrects the heart rate error.

In this schematic configuration, if the heart rate meter is used while performing exercise, there is a possibility that the heart rate sensor 2 moves away from the blood vessel of the person to be measured as a measuring target. This may induce a situation that the detected signal outputted from the detecting circuit 3 includes a part that does not show any output or a part where oscillation is caused by breaking-in of a disturbance light and the output is saturated. With such occurrence of the part showing no output or the part being saturated, an error may occur in the heart rate obtained from the heart rate detecting unit 4.

The heart rate variation detecting unit 5 detects a heart rate variation in a form of a time fluctuation of the heart rate. For example, a difference of the heart rate outputted from the heart rate detecting unit 4, between before and after a certain point of time, is obtained, and thereby detecting the heart rate variation. It is to be noted that this heart rate variation corresponds to a differential value of the heart rate, and if a function is available, which approximates the variation of the heart rate, the variation can be detected by a differential value of this function at a certain point of time.

As explained above with reference to FIGS. 2A-D, the heart rate error detecting and correcting unit 6 detects an error in the heart rate by detecting the heart rate variation error and by correcting the heart rate variation error (FIG. 2A to FIG. 2C). According to the correction of the heart rate variation error being detected, the heart rate error is corrected (FIG. 2C to FIG. 2D).

The heart rate counter 7 counts the heart rate based on the heart rate that has been corrected in the heart rate error detecting and correcting unit 6. The heart rate counted here indicates a heart rate after the error has been corrected. Therefore, it is possible to obtain an accurate heart rate.

Figure 4:
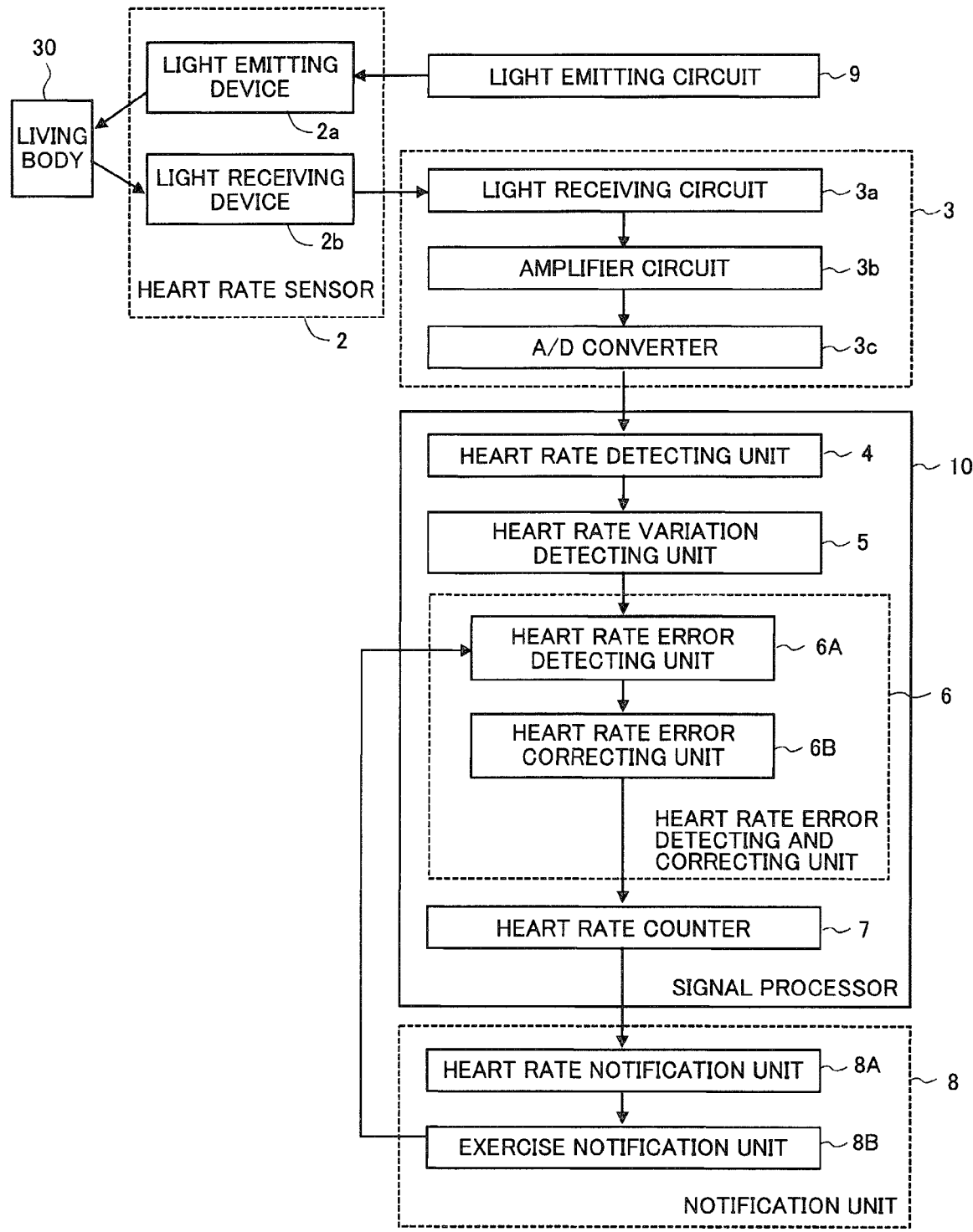
FIG. 4 is a diagram for explaining a configuration of the heart rate meter according to the present invention.

FIG. 4 is a diagram for explaining a configuration of the heart rate meter shown in FIG. 3. Here, there is shown an optical sensor as an example of the heart rate sensor 2.

The heart rate meter 1 includes the heart rate sensor 2 for obtaining heart beat information from the living body 30, a detecting circuit 3 for forming a detected signal from the output of the heart rate sensor 2, a signal processor 10 for subjecting the signal detected from the detecting circuit 3 to a signal processing and detecting the heart rate, and a heart rate notification unit 8A for notifying the heart rate being counted. It is to be noted that a notification unit 8 is made up of the heart rate notification unit 8A and an exercise notification unit 8B. The heart rate notification unit 8A displays the heart rate on a display unit, transmits the heart rate to other unit, or records the heart rate in a recording unit. On the other hand, the exercise notification unit 8B gives instructions to the test subject, as to starting or stopping the exercise. Accordingly, it is possible to apply load on the test object at a predetermined time. In addition, the exercise notification unit 8B transmits time information to the heart rate error detecting and correcting unit 6, at the exercise start time and the exercise end time. In the present invention, it is assumed that a type and magnitude of the load that is applied on the test subject are preset in the heart rate meter.

The signal processor 10 includes a heart rate detecting unit 4 for detecting a heart rate, a heart rate variation detecting unit 5 for detecting a variation from the heart rate being detected, a heart rate error detecting and correcting unit 6 for detecting an error and correcting the error of the heart rate based on the heart rate variation being detected, and heart rate counter 7 for counting the heart rate being corrected.

Figure 5:
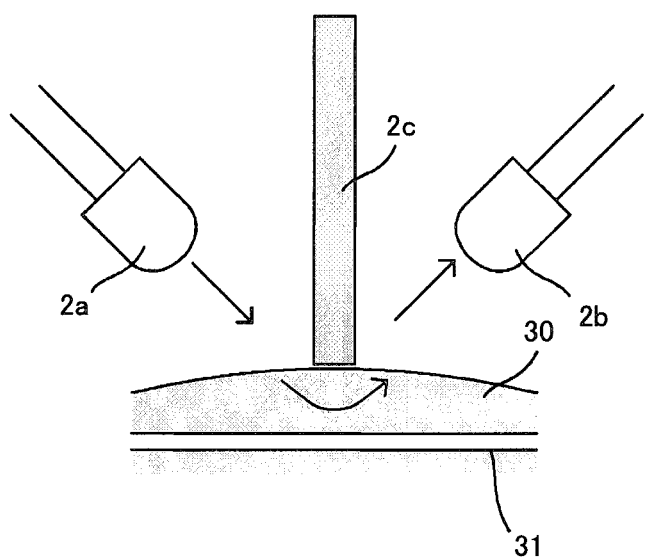
FIG. 5 is a schematic sectional view for explaining one configuration example of a heart rate sensor.

The heart rate sensor 2 includes a light emitting device 2a for irradiating a light on the living body 30, which is driven by a light emitting circuit 9, and a light receiving device 2b for receiving a light that is scattered or reflected by the living body 30, or a light being transmitted. FIG. 5 is a schematic sectional view for explaining one configuration example of the heart rate sensor 2, and the configuration example shows that a light is irradiated onto the living body 30 and a reflected light is detected. The light emitting device 2a and the light receiving device 2b are opposed to each other placing a shielding plate 2c therebetween, and they are located in a manner being symmetrical with respect to an irradiated point (not illustrated). Here, the shielding plate 2c blocks the light that is directly incident from the light emitting device 2a to the light receiving device 2b.

The light irradiated from the light emission device 2a to the living body 30 is scattered by the tissue in the living body 30 and the blood in the blood vessel 31, and emitted outwardly from the living body 30. The intensity of the light emitted from the living body 30 fluctuates according to the blood stream. The heart rate meter 1 according to the present invention detects the heart beat based on the variation of the light intensity that fluctuates according to the bloodstream.

The detecting circuit 3 includes a light receiving circuit 3a which receives the light signal obtained from the light receiving element 2b and converts the signal into a detected signal being an electrical signal, an amplifier circuit 3b which subjects the detected signal to signal amplification, and an A/D converter 3c that converts the signal into a digital signal.

The signal processor 10 includes, as described above, the heart rate detecting unit 4, the heart rate variation detecting unit 5, a heart rate error detecting and correcting unit 6, and a heart rate counter 7, and the signal processor 10 transmits the heart rate being obtained to the heart rate notification unit 8 for notifying the heart rate being counted.

The heart rate error detecting and correcting unit 6 includes a heart rate error detecting unit 6A for detecting a heart rate error, and a heart rate error correcting unit 6B for correcting the heart rate based on the heart rate error detected in the heart rate error detecting unit 6A. In addition, the heart rate notification unit 8 performs the notification of the heart rate, by any means of displaying, recording, and transmitting the heart rate, or any combination thereof.

Figure 6:
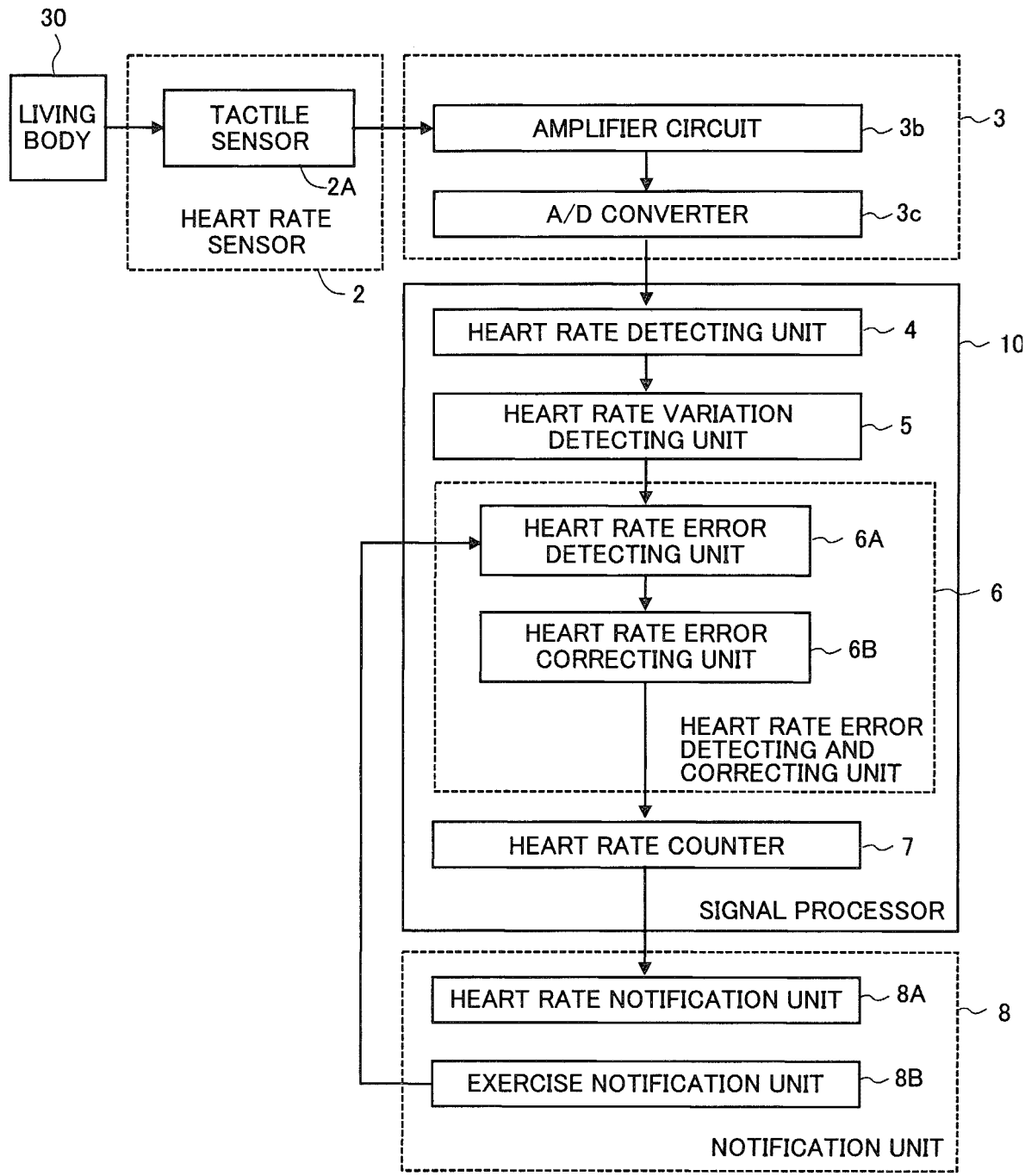
FIG. 6 is a diagram for explaining another configuration of the heart rate meter according to the present invention.

FIG. 6 is a diagram for explaining another configuration of the heart rate meter shown in FIG. 3. In this configuration example, a tactile sensor 2A is shown as an example of the heart rate sensor 2.

The heart rate meter 1 includes, as shown in FIG. 4 described above, the heart rate sensor 2, the detecting circuit 3, the signal processor 10, and the notification unit 8. A detected signal from the tactile sensor 2A serving as the heart rate sensor 2 is subjected to the signal amplification by the an amplifier circuit 3b in the detecting circuit 3, and converted into a digital signal by the A/D converter 3c.

In this configuration example, the tactile sensor 2A is provided as the heart rate sensor 2. Here, the tactile sensor 2A generically represents a sensor for detecting an oscillation emitted from a living body, and by way of example, this sensor detects a heart rate by detecting a pulse of arterial vessel within the living body.

Figure 7:
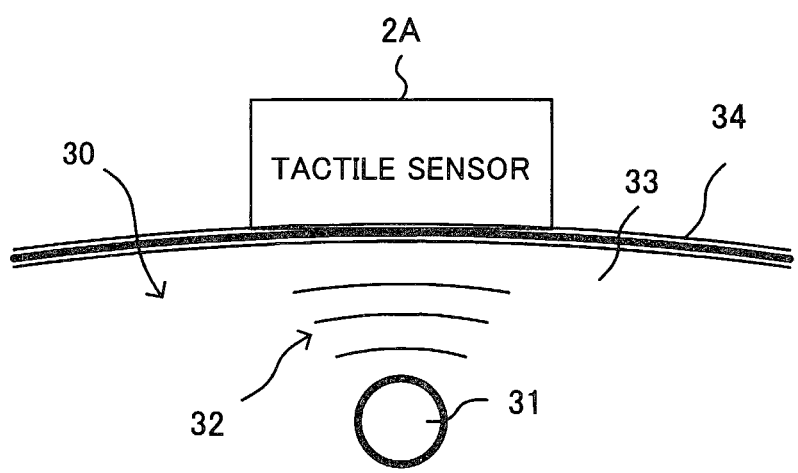
FIG. 7 is a schematic sectional view for explaining another configuration example of the heart rate sensor.

FIG. 7 is a schematic sectional view for explaining one configuration example of the tactile sensor 2A. The arterial vessel 31 within the living body oscillates, in synchronization with the pulse, according to fluctuations of the blood flowing in the blood vessel. The oscillation of the arterial vessel is propagated in the body tissue 33 in a form of oscillatory wave. The tactile sensor 2A is mounted on the skin in such a manner as brought into contact therewith, so as to detect the oscillatory wave propagating in the body tissue 33. The oscillatory wave is detected in a form of variation of pressure or variation of oscillation.

As the tactile sensor 2A, various sensors are available depending on a manner how to detect the oscillatory wave. For example, if a pressure sensor is employed as the tactile sensor 2A, an oscillatory wave is detected as variation of pressure. Alternatively, if an oscillation sensor is employed as the tactile sensor 2A, the oscillatory wave is detected as variation of oscillation. The variation of oscillation being detected is a variation in amplitude, frequency, or the like.

The tactile sensor 2A detects via the skin, an oscillatory wave propagating through the tissue 33 of the living body. Therefore, the tactile sensor 2A is mounted in proximity to a portion to be measured where a pulse of the living body can be detected. The detection sensitivity of the tactile sensor 2A can be improved by bringing it into contact with the skin 34 in proximity to the portion to be measured, and further, by pressing the tactile sensor 2A against the skin 34, the detection sensitivity can be enhanced more.

The tactile sensor 2A detects an oscillatory wave that fluctuates according to a bloodstream, the detecting circuit 3 subjects a detected signal to a signal amplification in the amplifier circuit 3b, and the A/D converter 3c converts the amplified signal into a digital signal.

It is to be noted here that the configuration and signal processing operations of the heart rate detecting unit 4, the heart rate variation detecting unit 5, the heart rate error detecting and correcting unit 6, and the heart rate counter 7 within the signal processor 10, the configuration and the signal processing of the heart rate notification unit 8, and the operations of each unit, are the same as those explained above with reference to FIG. 4. Therefore, redundant explanation will not be given here.

If an optical sensor is employed as the heart rate sensor, a portion for detecting a heart rate signal can be specified within a narrow range, and a heart rate state at a specified position can be detected. Alternatively, if a tactile sensor is employed as the heart rate sensor, a heart rate signal can be obtained from a wide range, and therefore, a high precision in deciding the position for mounting the heart rate sensor is not necessary. In addition, it is possible to reduce a faulty detection due to a displacement of the sensor while being used.

Figure 8:
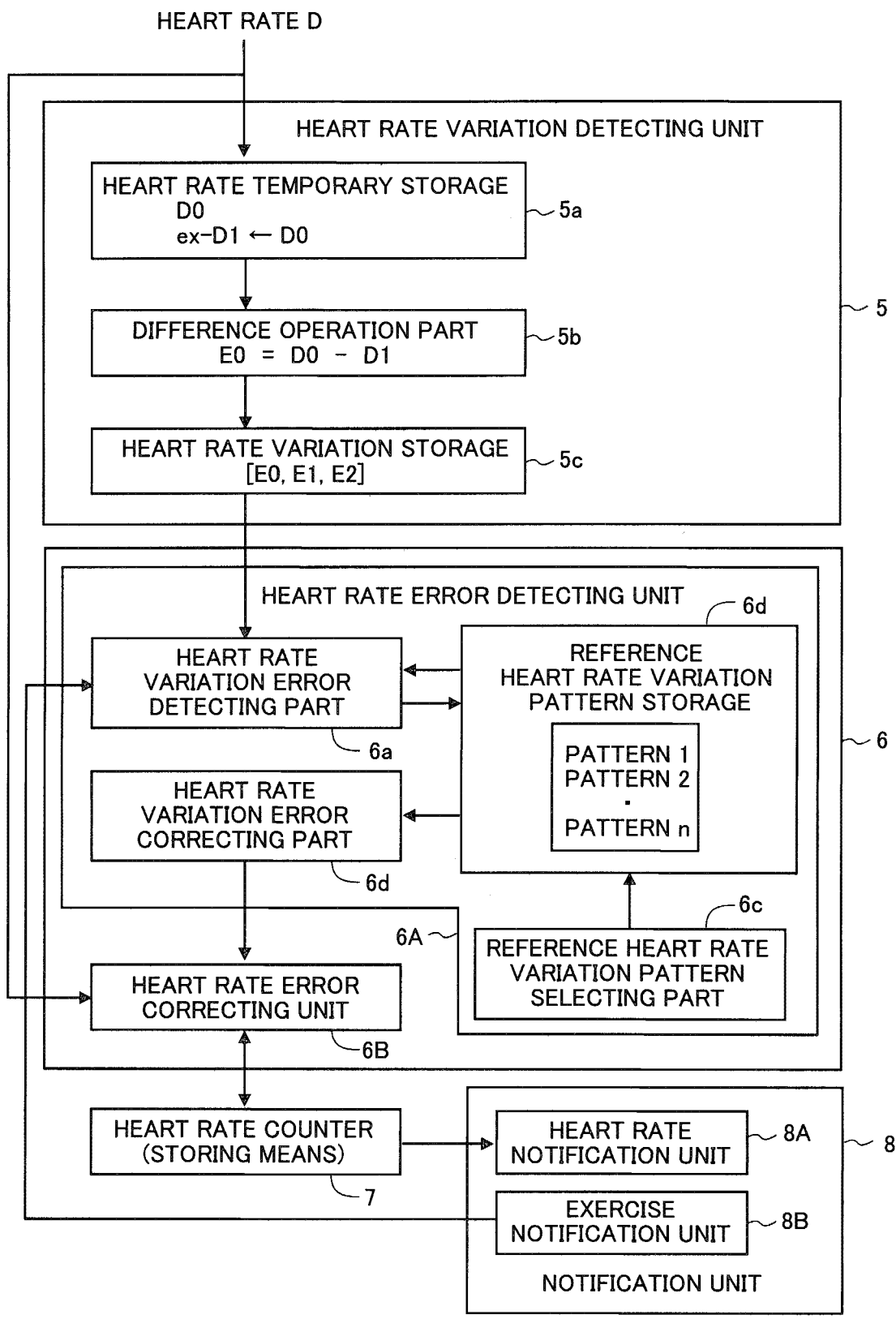
FIG. 8 is a diagram for explaining a configuration example of the heart rate variation detecting unit and the heart rate error detecting unit.

Next, with reference to FIG. 8, a configuration example of the heart rate variation detecting unit 5 and a configuration example of the heart rate error detecting unit 6A within the heart rate error detecting and correcting unit 6 will be explained.

Firstly, the configuration example of the heart rate variation detecting unit 5 will be explained. The heart rate variation detecting unit 5 includes a heart rate temporary storage 5a for inputting and storing the heart rate D detected by the heart rate detecting unit 4, a difference operation part 5b for calculating a heart rate variation E based on the heart rate D stored in the heart rate temporary storage 5a, and a heart rate variation storage 5c for storing the heart rate variation obtained in the difference operation part 5b.

The heart rate temporary storage 5a stores the heart rate D being inputted as a current heart rate D0, and simultaneously rewrites a previously stored current heart rate D0 as a previous heart rate D1. In the heart rate temporary storage 5a, the current heart rate D0 and the previous heart rate D1 are rewritten every time when a new heart rate D is inputted. The previous heart rate D1 before rewritten is abandoned.

The difference operation part 5b obtains a heart rate variation value E0 by a difference operation between the current heart rate D0 and the previous heart rate D1 (E0=D0−D1). This difference operation aims at obtaining a variation of the heart rate that indicates fluctuation within a predetermined period of time.

In the heart rate variation storage 5c, multiple heart rate variation values E obtained in the difference operation part 5b are stored at every different points of time. Here, the heart rate variation storage 5c stores three heart rate variation values [E0, E1, E2]; the current heart rate variation value E0, the previous heart rate variation value E1, and the two-times previous heart rate variation value E2. The stored heart rate variation values are updated every time when the heart rate variation value E is computed in the difference operation part 5b, and the oldest heart rate variation value E2 is abandoned and replaced by the new heart rate variation value E2 in sequence.

With the procedure above, the heart rate variation storage 5c stores three heart rate variation values [E0, E1, E2], the values being successive from the present to the past, at a certain point of time every elapsed time period.

In the present invention, multiple heart rate variation values are used as a variation pattern of the heart rate variation, and thereby detecting an error in the heart rate variation. It is to be noted that the number of the heart rate variation values is assumed as three in the example here, but the number is not limited to three and any number is applicable.

If the number of the successive heart rate variation values is set to two, the number of patterns that enables the detection of a heart rate variation error is limited, and therefore, the detection precision may be decreased. If the number of the heart rate variation values is increased, the detection precision for detecting an error in the heart rate variation is increased, but a longer operation time is required for detecting an error. In addition, at the initial stage, there is not enough number of heart rate variation values that are required for detecting an error, and therefore, it may take a long time until a first heart rate variation is detected. Consequently, there is a possibility that a heart rate variation error at the initial stage is missed. Therefore, those points above are considered in setting of the number of the heart rate variation values being successive.

The configuration example of the heart rate variation detecting unit 5 as described above shows that the heart rate variation is detected every time when the heart rate is obtained. However, the detection of the heart rate variation may be conducted every time when multiple heart rates are acquired.

Next, a configuration example of the heart rate detecting unit 6A of the heart rate error detecting and correcting unit 6 will be explained. In FIG. 8, the heart rate error detecting unit 6A includes a heart rate variation error detecting part 6a, a reference heart rate variation pattern storage 6b, a reference heart rate variation pattern selecting part 6c, and a heart rate variation error correcting part 6d.

The heart rate variation error detecting part 6a detects whether or not there is an error in the heart rate variation that is detected in the heart rate variation detecting unit. In this error detection, a variation pattern of the heart rate variation of a target heart beat waveform is compared with a variation pattern of the reference heart rate variation that is obtained in advance.

If there is a coincidence between the target heart rate variation pattern and the variation pattern of the reference heart rate variation, it is determined that there is no error in the heart rate variation. If the target heart rate variation pattern does not match the reference heart rate variation pattern, it is determined that there is an error in the heart rate variation.

Figure 9A:
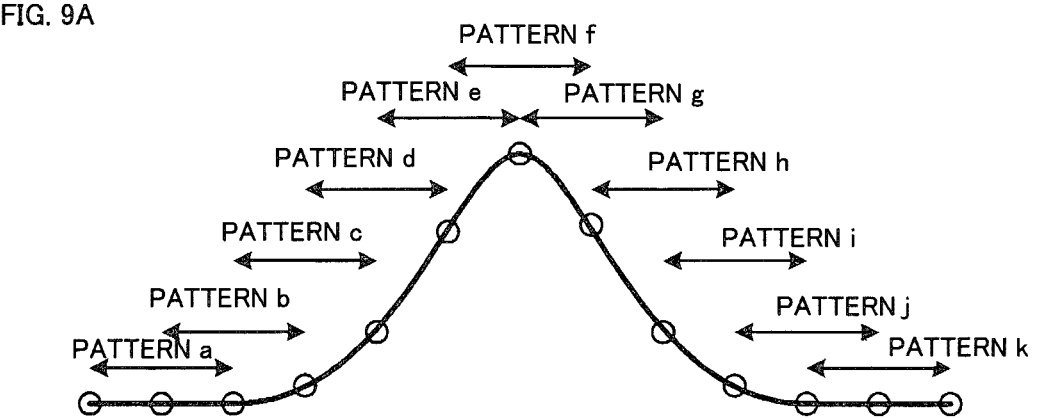
FIGS. 9A and B illustrate examples of the heart rate variation patterns.
Figure 9B:
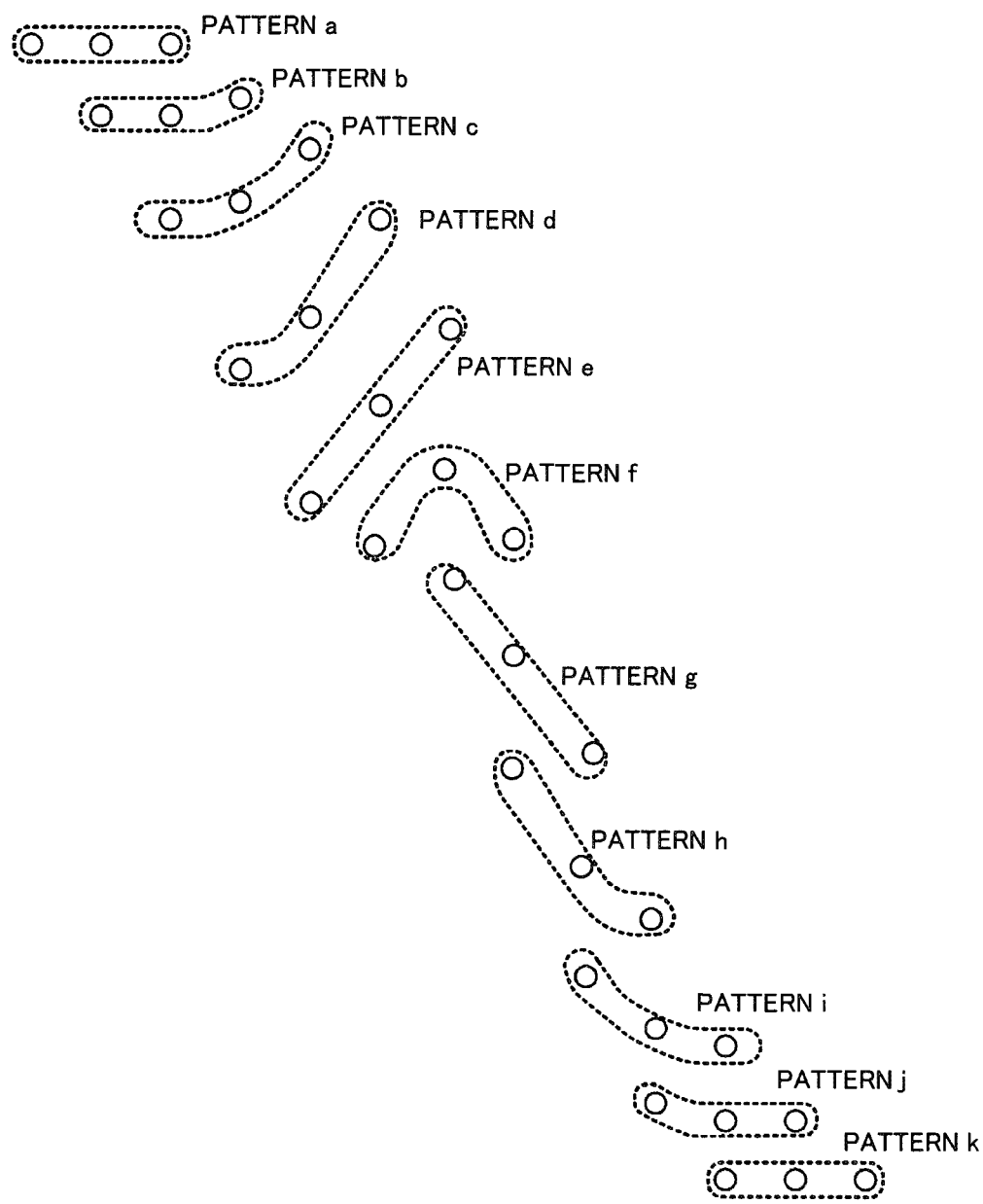

The heart rate variation pattern shows differences depending on the elapsed time of the heart rate variation. FIGS. 9A and B illustrate one example of the heart rate variation patterns. The heart rate variation patterns a to k (FIG. 9B) are obtained by partitioning the waveform of the heart rate variation in units of a predetermined time width (the time widths indicated by arrows in the figure), and a fluctuating state of the heart rate variation values within this time width are extracted in a form of the heart rate variation pattern. Here, there is shown an example that the heart rate variation pattern is formed by three successive heart rate variation values.

A heart rate variation pattern used for the comparison is determined in advance and stored, as the reference heart rate variation pattern. This reference heart rate variation pattern shows different patterns depending on the elapsed time of the heart rate variation, similar to the case of the heart rate variation patterns. Therefore, the reference heart rate pattern storage 6b stores multiple patterns. Accordingly, when the heart rate variation pattern is compared with the reference heart rate variation pattern, multiple reference heart rate variation patterns may exist, which do not match the heart rate variation pattern.

If multiple reference heart rate variation patterns exist, which do not match the target heart rate variation patterns, there is a possibility that the target heart rate variation pattern includes an error, and there is also a possibility as the following; the target heart rate variation pattern does not include any error, but simply, there is a discrepancy in the elapsed time of the comparison targets, and therefore, the result is obtained just by the comparison between the heart rate variation patterns that originally should not be the comparison targets.

In general, when the elapsed time is not consistent between the comparison targets, many of the heart rate variation values of the heart rate variation patterns do not coincide with one another. On the other hand, if the elapsed time of the comparison target is made correspond to that of another comparison target, and the heart rate variation patterns are appropriate comparison targets, there has to be agreement between the respective heart rate variation values of the heart rate patterns, if there is no error. If there is an error, the heart rate variation values at the error point are different from each other.

In view of the situation above, if there are multiple reference heart rate variation patterns that do not match the target heart rate variation pattern, the error detection is performed, considering the size of quantity of the unmatched heart rate variation values. For example, when a large number of heart rate variation values do not agree with each other, it is determined that the reference heart rate variation pattern is not the comparison target, and when the number of the heart rate variation values that do not show the agreement is small, it is determined that the reference heart rate variation pattern is suitable as the comparison target, and the target heart rate variation includes an error. A set value for the quantity of the heart rate variation values, which is used as this determination, is configured in advance.

In addition, in the heart rate variation pattern where an error is detected, a position of the heart rate variation value that does not show the agreement represents a position where the heart rate variation is wrong, and accordingly, it is possible to detect the position of the error.

A heart rate is measured under the same measuring condition, such as applying certain loads onto multiple test subjects in advance. Then, based on the multiple measuring results, a common heart rate variation pattern is stored as the reference heart rate variation pattern in the reference heart rate variation pattern storage 6b. As shown in FIGS. 9A and B described above, this reference heart rate variation pattern includes various patterns depending on the elapsed time of the heart rate variation.

The heart rate variation error detecting part 6a introduces a variation value of the target heart rate variation from the heart rate variation storage 5c, simultaneously reads a reference heart rate variation pattern from the reference heart rate variation pattern storage 6b, and then compares the variation values of these variation patterns with each other. It is to be noted here that the comparison of the variation values are performed, by comparing the heart rate variation values with the reference heart rate variation values at multiple points of time previous to the target point of time, and thereby detecting an error at the target point of time.

The heart rate variation error detecting part 6a is allowed to read the reference heart rate variation pattern from the reference heart rate variation pattern storage 6b, at the timing when a signal is outputted from the exercise notification unit 8B. The exercise notification unit 8B has a configuration for notifying the test subject of starting of load application, and the heart rate variation starts fluctuation from the point of time when the load is applied on the test subject.

Therefore, it is possible to know when the fluctuation in the heart rate variation is started, by monitoring the signal from the exercise notification unit 8B, and thereby eliminating a noise during non-exercise conditions.

At the time of exercise start, the heart rate variation error detecting part 6a reads from the reference heart rate variation pattern storage 6b, a reference heart rate variation pattern that appears when the execution is started. When the exercise is finished, the heart rate variation error detecting part 6a reads from the reference heart rate variation pattern storage 6b, a reference heart rate variation pattern that appears when the execution is finished.

In addition, in the comparison operation, when multiple reference heart rate variation patterns exist, each of which has a possibility as being a pattern that the target heart rate variation values may take, it is possible to select an appropriate pattern from the multiple reference heart rate variation patterns stored in the reference heart rate variation pattern storage 6b. This selection can be performed by the heart rate variation pattern selecting part 6c. For example, by using the elapsed time of the heart rate variation as a parameter, it is possible to select an available pattern that may be taken by the evaluation target heart rate variation.

By selecting the reference heart rate variation pattern, there is an effect as the following; it is possible to prevent that a heart rate variation pattern is erroneously detected as a matched pattern, which is far from being detected according to the elapsed time of the heart rate variation. There is a further effect that the transaction volume of the pattern comparison can be reduced, which is performed in the heart rate variation error detecting part 6a.

In order to correct the heart rate variation error and the heart rate error, information for making the correction is needed. However, as described above, if a motion artifact occurs when the heart rate sensor becomes detached from the measuring part, the heart beat waveform does not include any heart rate information, and therefore, it is difficult to make the correction based on the heart beat waveform. In view of this problem, the present invention makes use of the heart rate information held by the reference heart rate variation pattern, which has been used in the heart rate error detecting unit 6A, and thereby compensates lost heart rate information.

The heart rate variation error correcting part 6d extracts a heart rate variation value corresponding to the lost heart rate, from the heart rate variation values of the reference heart rate variation pattern, and by using the heart rate variation value being extracted, an error of the heart rate variation is corrected. More particularly, the heart rate variation error correcting part 6d assumes a target point of time detected by the heart rate variation error detecting part 6a as an error position. Then, a heart rate variation value associated with the target point is read out from the reference heart rate variation pattern stored in the reference heart rate variation pattern storage 6b. The readout variation value substitutes for the heart rate variation value determined as an error, thereby correcting the error in the heart rate variation.

Furthermore, the heart rate correcting unit 6B obtains a heart beat position based on the heart rate error position detected in the heart rate variation error detecting part 6a. In addition, the heart rate is corrected according to the number of errors in the heart rate variation, which is detected in the heart rate variation error correcting part 6d.

Figure 10:
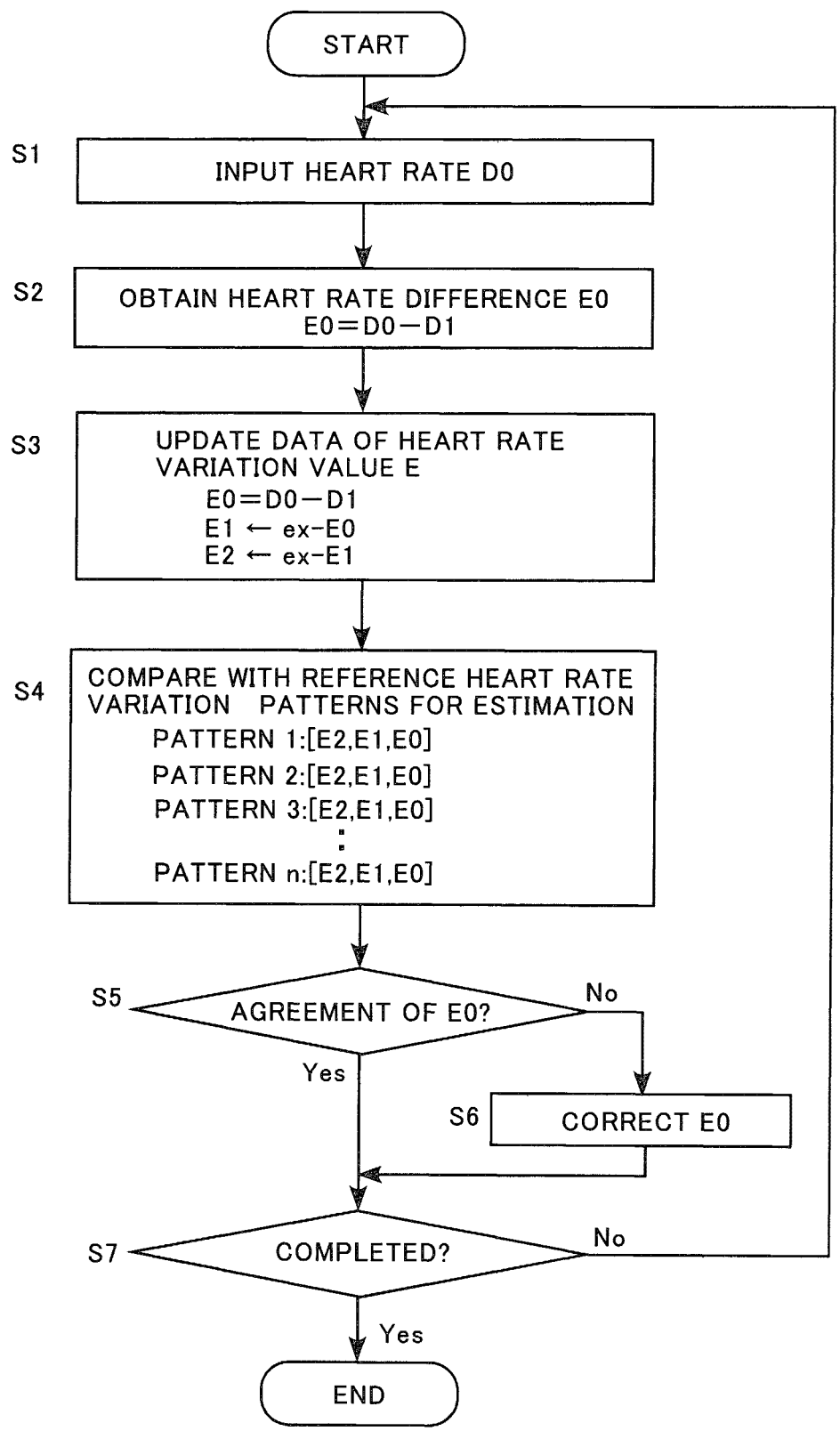
FIG. 10 is a flowchart to explain an operation example of the heart rate error detecting and correcting unit.

Hereinafter, an operation example of the heart rate error detecting and correcting unit 6 will be explained, with reference to the flowchart in FIG. 10, the heart rate variation example in FIG. 11, and an operational illustration in FIG. 12.

Firstly, the heart rate temporary storage 5a inputs a heart rate D from the heart rate detecting unit 4, stores the inputted heart rate D as a current heart rate D0, and simultaneously rewrites the current heart rate D0 previously stored as the previous heart rate D1 (S1).

The difference operation part 5b performs a difference operation (E0=D0−D1) between the current heart rate D0 and the previous heart rate D1 (S2).

The heart rate variation value obtained by the operation is stored as the heart rate variation value E0 at the current time, and the heart rate variation value E0 having been the current-time heart rate variation value at the previous time is stored as the previous heart rate variation value E1. In addition, the heart rate variation value E1 that has been the previous heart rate value at the previous time is stored as the two-times previous heart rate variation value E2. Accordingly, there are stored three heart rate variation values [E0, E1, E2]; the current time heart rate variation value E0, the previous heart rate variation value E1, and the two-times previous heart rate variation value E2 (S3).

Next, a reference heart rate variation pattern used for the heart rate variation error detecting and correcting is estimated, and by use of the estimated reference heart rate variation pattern, error detection and error correction are performed.

In order to estimate the reference heart rate variation pattern that is used for determination, out of multiple reference heart rate variation patterns, the heart rate variation pattern obtained in S3 step is compared with each of the reference heart rate patterns.

Figure 11:
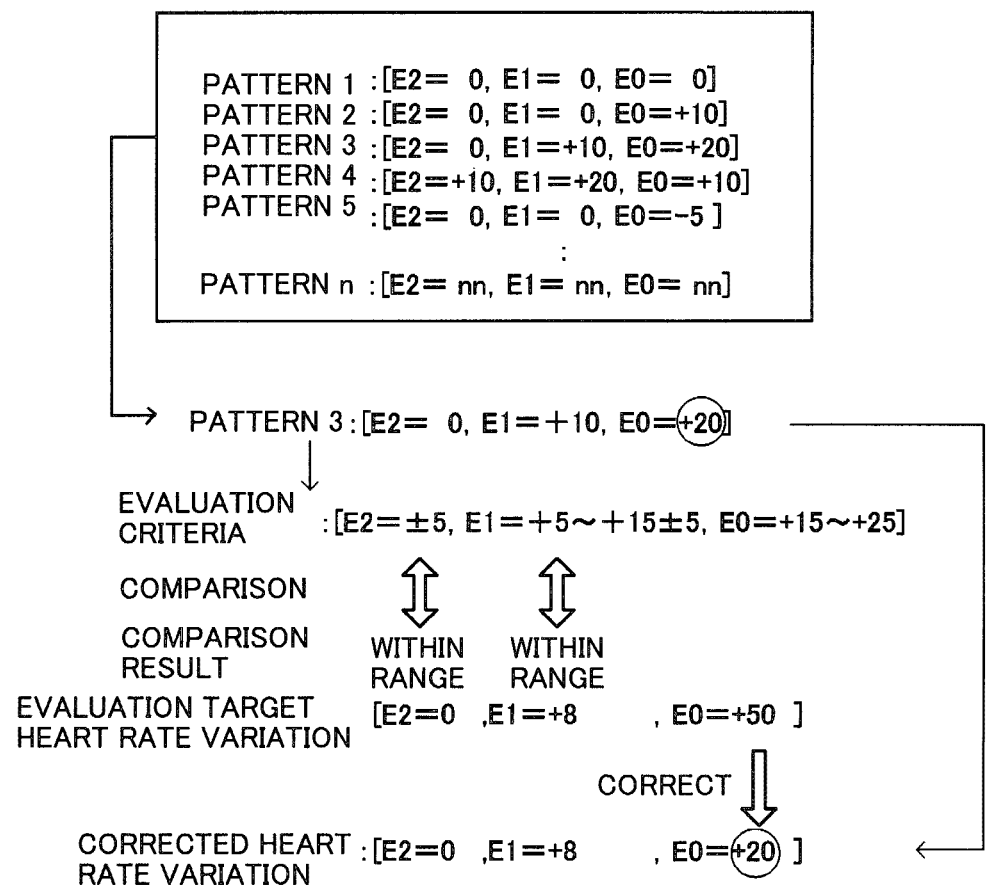
FIG. 11 illustrates an example of the heart rate variation in the operation example of the heart rate error detecting and correcting unit.

By way of example, FIG. 11 shows that the heart rate variation error detection and correction are performed, setting the reference heart rate variation patterns as the following, providing margins for judgment of ±5, respectively for E1 and E2;

Pattern 1: [E2, E1, E0]=[0, 0, 0]
Pattern 2: [E2, E1, E0]=[0, 0, +10]
Pattern 3: [E2, E1, E0]=[0, +10, +20]
Pattern 4: [E2, E1, E0]=[+10, +20, +10]
Pattern 5: [E2, E1, E0]=[0, 0, −5]
.
.
.
Pattern n: [E2, E1, E0]=[nn, nn, nn]

Here, it is to be noted that E0 represents a heart rate variation at the target point of time for evaluation, E1 represents a heart rate variation at the point of time one-time previous to the target point of time, and E2 represents a heart rate variation at the point of time two-times previous to the target point of time.

Estimation of the reference heart rate variation pattern is performed by comparing the values of E1 and E2. For example, in this setting example, if the evaluation target heart rate variation pattern [E2, E1, E0]=[0, +8, +50] (FIG. 12B), the evaluation criteria of E2 is ±5 and the evaluation criteria of E1 is +5 to +15 as to the pattern 3 ([E2, E1, E0]=[0, +10, +20]). Therefore, each value of the evaluation target heart rate variation, E2=0, E1=+8, fits into the each evaluation range. Accordingly, the pattern 3 is estimated as the reference heart rate variation pattern.

Figure 12A:
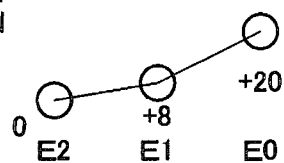
FIGS. 12A, B, C, D and E show illustrations to explain operation examples of the heart rate error detecting and correcting unit.
Figure 12B:
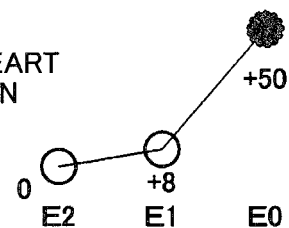
Figure 12C:
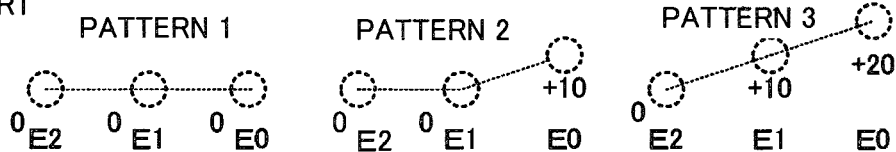
Figure 12D:
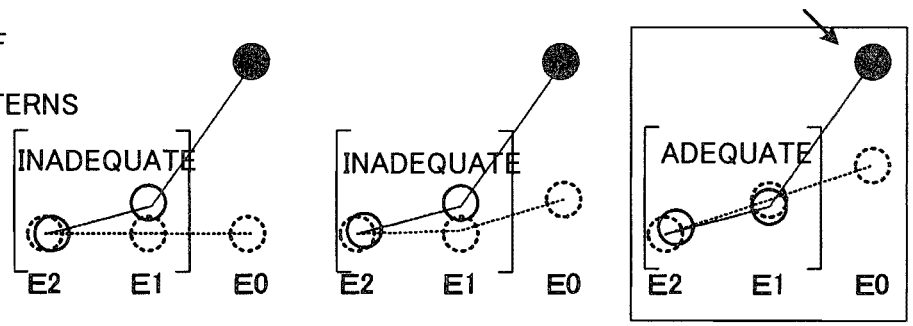
Figure 12E:
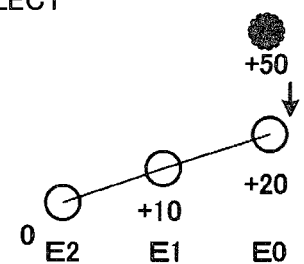

In FIG. 12C, the pattern 1 or pattern 2 may also be considered as a candidate for the reference heart rate variation pattern. However, the evaluation criteria of E2 as to the pattern 1 ([E2, E1, E0]=[0, 0, 0]) is ±5 and the evaluation criteria of E1 is ±5. Therefore, the evaluation target heart rate variation value E1=+8 does not fit into the evaluation criteria. The evaluation criteria for E2 as to the pattern 2 ([E2, E1, E0]=[0, 0, +10]) is ±5 and the evaluation criteria of E1 is ±5, and therefore, the evaluation target heart rate variation value E1=+8 does not fit into the evaluation criteria either (FIG. 12D).

Therefore, as described above, the pattern 3 having the values of [E1, E2] that fit into the evaluation criteria is estimated as the reference heart rate variation pattern (S4).

Next, the value of E0 of the pattern 3 estimated as the reference heart rate variation pattern is compared with the value of E0 of the evaluation target heart rate variation pattern. If there is not a match (S5), the value of E0=+50 of the evaluation target heart rate variation pattern is replaced by the value of E0=+20 of the reference heart rate variation pattern 3, whereby the correction is performed. According to this correction, it is possible to obtain the heart rate variation pattern (E2, E1, E0)=[0, +8, +20] (FIG. 12E) (S6).

In the comparison step of S5, if E0 of the reference heart rate variation pattern 3 agrees with E0 of the evaluation target heart rate variation pattern, it is determined that there is no error in the heart rate variation value of the evaluation target, and thus there is no need of correction. The steps S1 to S6 described above are repeated every time when the heart rate variation is obtained (S7).

Next, with reference to FIG. 13 to FIG. 17, an example of hardware configuration will be explained, which implements the processing of the aforementioned heart rate error detecting unit.

Figure 13:
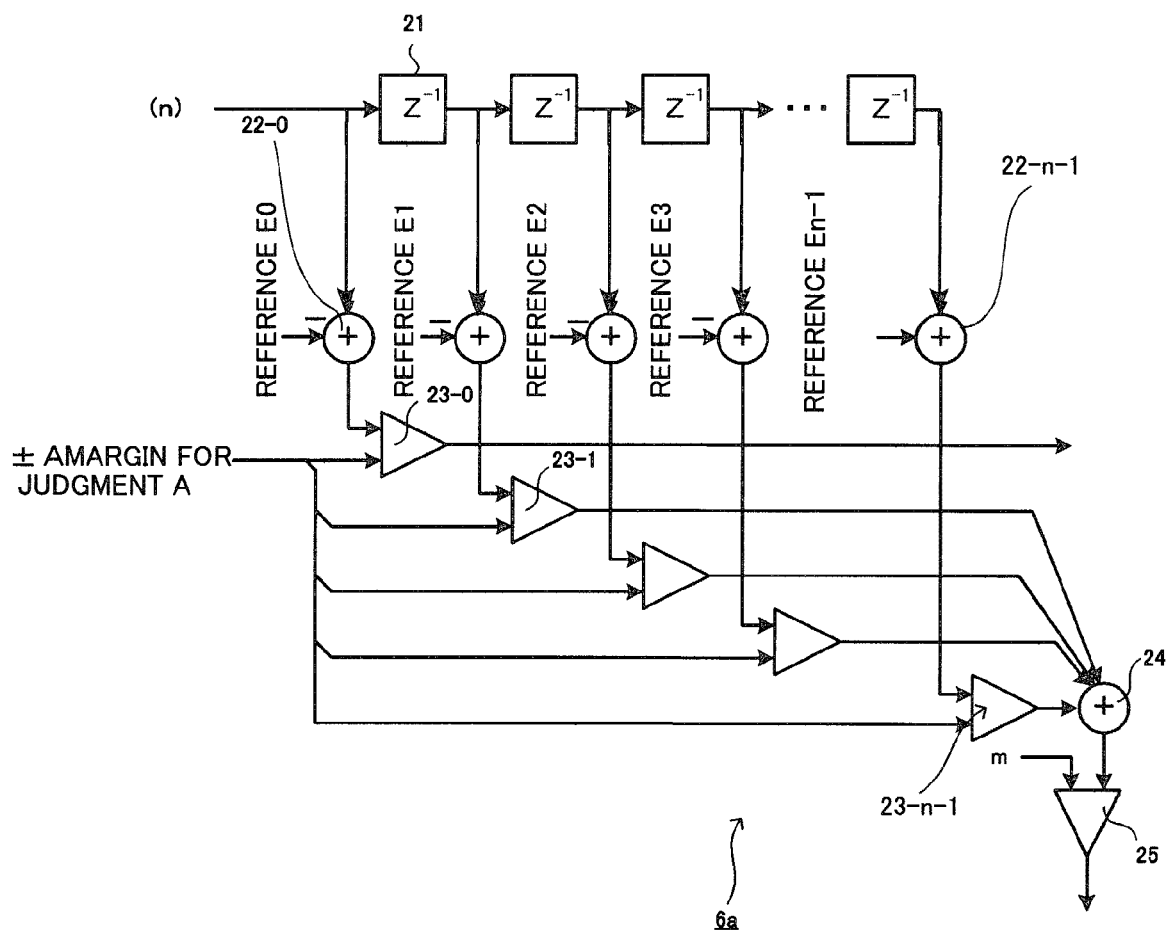
FIG. 13 shows an example of circuit configuration of the heart rate error detecting unit.

FIG. 13 is an example of a circuit configuration of the heart rate error detecting unit. The circuit configuration example as shown in FIG. 13 is made up of a delay circuit 21, an adders 22 and 24, a comparators 23 and 25, and the like.

The delay circuits 21 are connected sequentially, the number of which is associated with the number of heart rate n constituting the heart rate variation pattern (e.g., (n−1)), and n adders 22 are connected to the input terminal and to the output terminals of the respective delay circuits 21. Each adder 22 is configured so that the heart rate variation values E0 to En−1 of the reference heart rate variation pattern are subtracted. Outputs from the adders 22 are respectively inputted in the comparators 23, and a comparison is made assuming the margin for judgment A as the evaluation criteria. The aforementioned processes by the adders 22 and the comparators 23 correspond to the steps of S4 and S5 in the flowchart described above.

The output from the comparator 23-0 obtained by the comparing process as to the output from the adder, which is connected to the input terminal, represents a difference between the heart rate variation E0 and the reference value. The output from the comparator 23-1 to 23-n−1 obtained by the respective comparing processes as to the outputs from the adders, which are connected to the delay units respectively, represent the differences between the heart rate variations E1 to En and the reference values, respectively.

Then, the adder 24 combines the outputs from the comparators 23-1 to 23-n−1 each making comparison as to the output from each of the adders respectively connected to the delay units, and obtains an output corresponding to the total number indicating how many heart rate variation values fit to each other. The comparator 25 compares the total number with the set number m (e.g., (n−1)), and thereby determining whether the reference heart rate variation pattern is adequate or inadequate.

With this circuit configuration, according to the output from the comparator 25, it is possible to confirm the reference heart rate variation pattern is adequate, and an error can be detected according to the output from the comparator 23-0. If there is no output obtained from the comparator 23-0, it is possible to determine that there is no error.

FIG. 13 illustrates an example showing that n pieces of heart rate variation values in the heart rate, being successive, constitute the heart rate variation pattern. Here, the case where n=3 will be explained, with reference to FIG. 14 showing the circuit configuration diagrams and FIG. 15 showing the heart rate variation patterns.

Both of FIGS. 14A-C and FIGS. 15A-C illustrate examples when ([E2, E1, E0]=[0, +10, +20]) is set as the reference heart rate variation pattern.

Figure 14A:
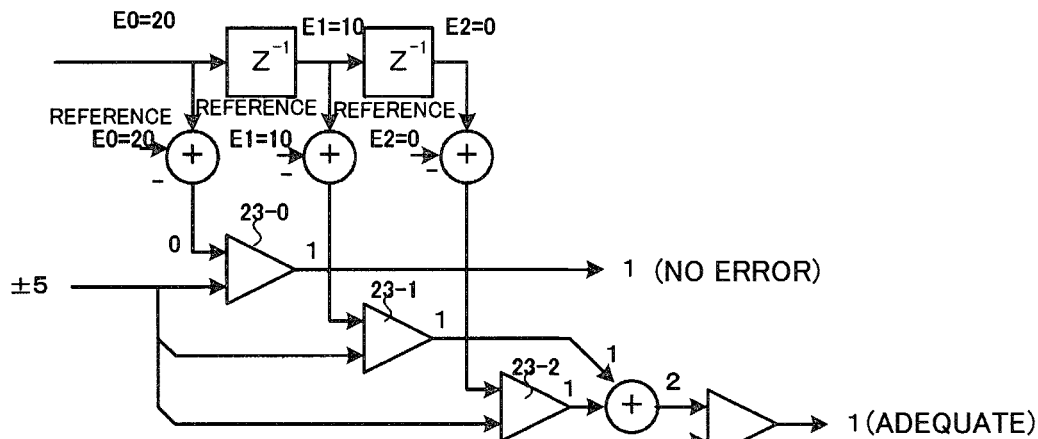
FIGS. 14A, B and C show examples of circuit configuration of the heart rate error detecting unit.
Figure 15A:
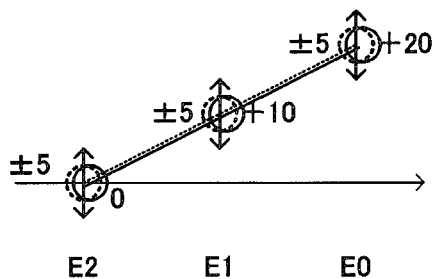
FIGS. 15A, B and C show illustrations for explaining the heart rate variation patterns.

FIG. 14A and FIG. 15A illustrate the case where ([E2, E1, E0]=[0, +10, +20]) is inputted as the evaluation target heart rate variation pattern. This example represents the case where there is no error in the evaluation target heart rate variation. According to the circuitry example of FIG. 14A, "1" is outputted from the comparator 23-0, indicating that it is judged as "there is no error". It is to be noted that in the example here, the comparator is designed to output "1", if the result fits into the range of the evaluation criteria.

Furthermore, the value "1" is outputted from each of the comparators 23-1 and 23-2 and these values are added in the adder 24, and the value "2" is outputted. The comparator 25 compares the output "2" from the adder 24 with the set value "2", and outputs the value "1". This output "1" represents that the reference heart rate variation pattern is adequate.

Figure 14B:
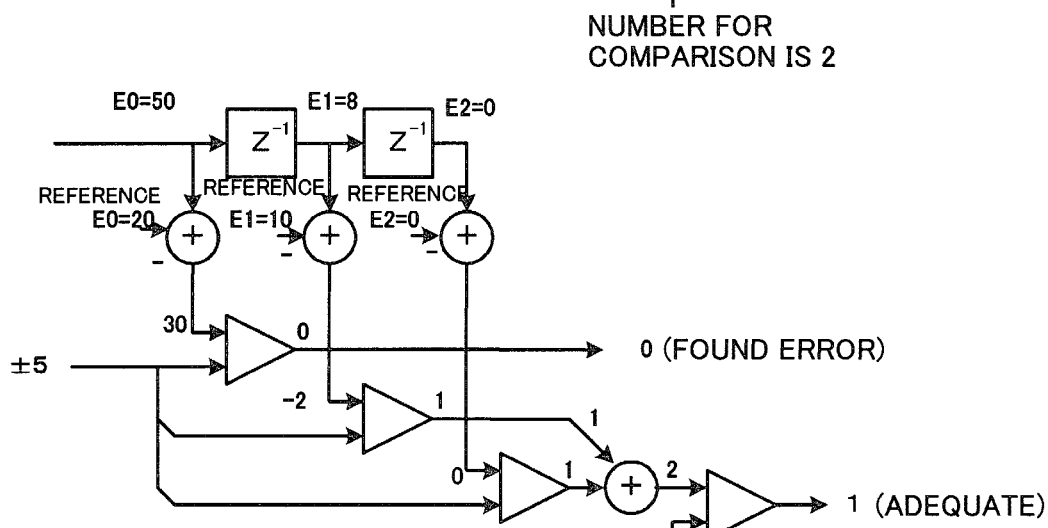
Figure 15B:
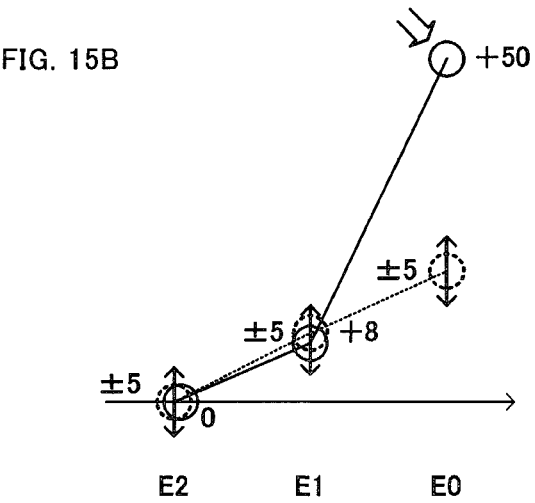

FIG. 14B and FIG. 15B illustrate the case where ([E2, E1, E0]=[0, +8, +50]) is inputted as the evaluation target heart rate variation pattern. This example represents the case where there is an error in the evaluation target heart rate variation. According to the circuitry example of FIG. 14B, "0" is outputted from the comparator 23-0, indicating that it is judged as "there is an error". It is to be noted that in the example here, the comparator is designed to output "0", when the result is out of the range of the evaluation criteria.

The value "1" is outputted from each of the comparators 23-1 and 23-2 and these values are added in the adder 24, and the value "2" is outputted. The comparator 25 compares the output "2" from the adder 24 with the set value "2", and outputs the value "1". This output "1" represents that the reference heart rate variation pattern is adequate.

Figure 14C:
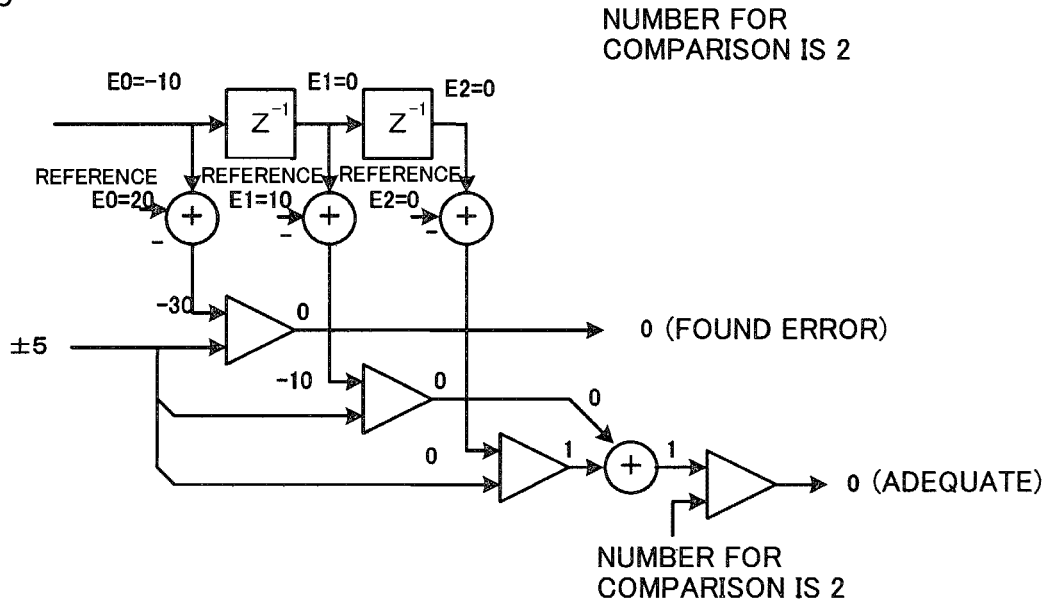
Figure 15C:
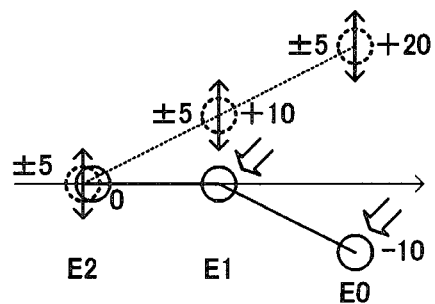

Next, FIG. 14C and FIG. 15C illustrate the case where ([E2, E1, E0]=[0, 0, −10]) is inputted as the evaluation target heart rate variation pattern. This example represents the case where the reference heart rate variation pattern is inadequate. According to the circuitry example of FIG. 14C, "0" is outputted from the comparator 23-0, indicating that it is judged as "there is an error".

In addition, the value "0" is outputted from the comparator 23-1, the value "1" is outputted from the comparator 23-2, and then, the value "1" obtained by addition in the adder 24 is outputted. The comparator 25 compares the output "1" from the adder 24 with the set value "2", and outputs the value "0". This output "0" represents that the reference heart rate variation pattern is inadequate.

Figure 16:
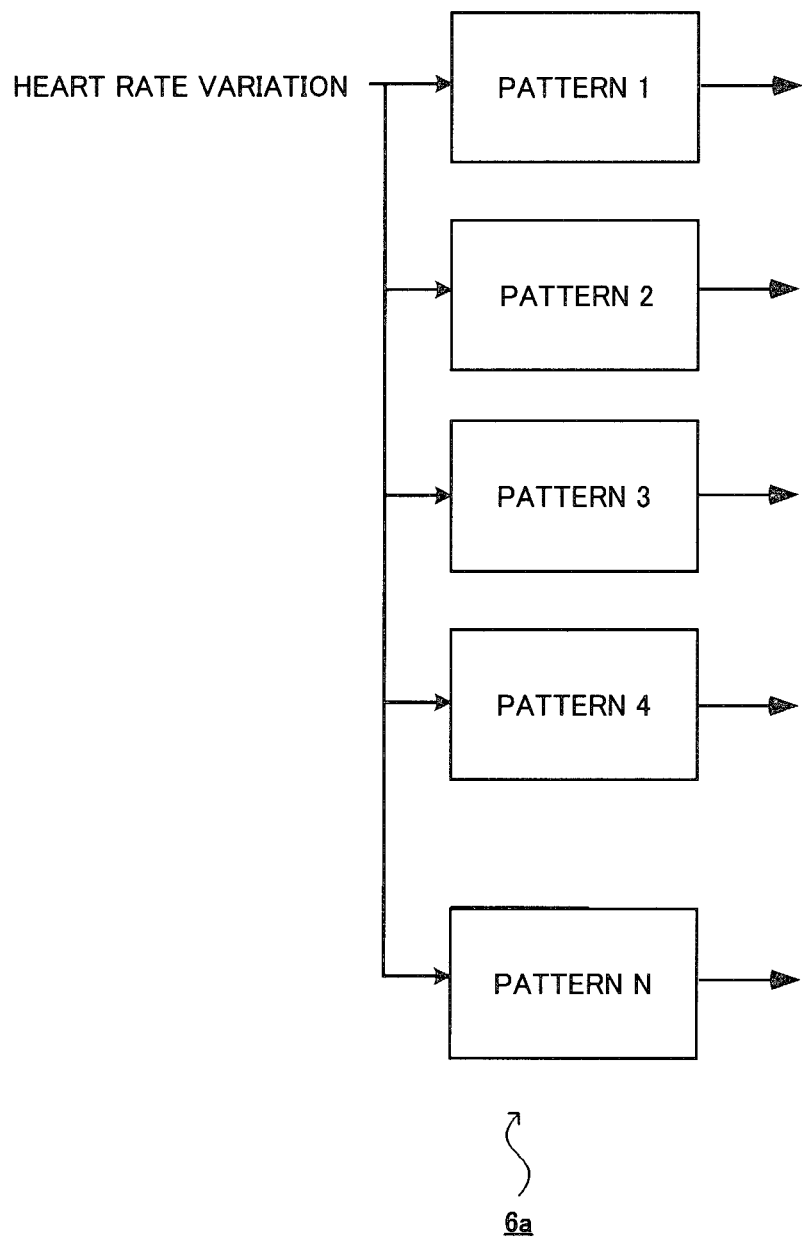
FIG. 16 illustrates one example of parallel-connected circuit configuration of the heart rate error detecting unit.

As shown in FIG. 16, the heart rate variation error detecting part 6a is configured in such a manner that the circuits having the aforementioned configuration are prepared respectively for each of the reference heart rate variation patterns, connected in parallel, and the heart rate variation is inputted in parallel in each of the circuits of respective patterns.

Figure 17:
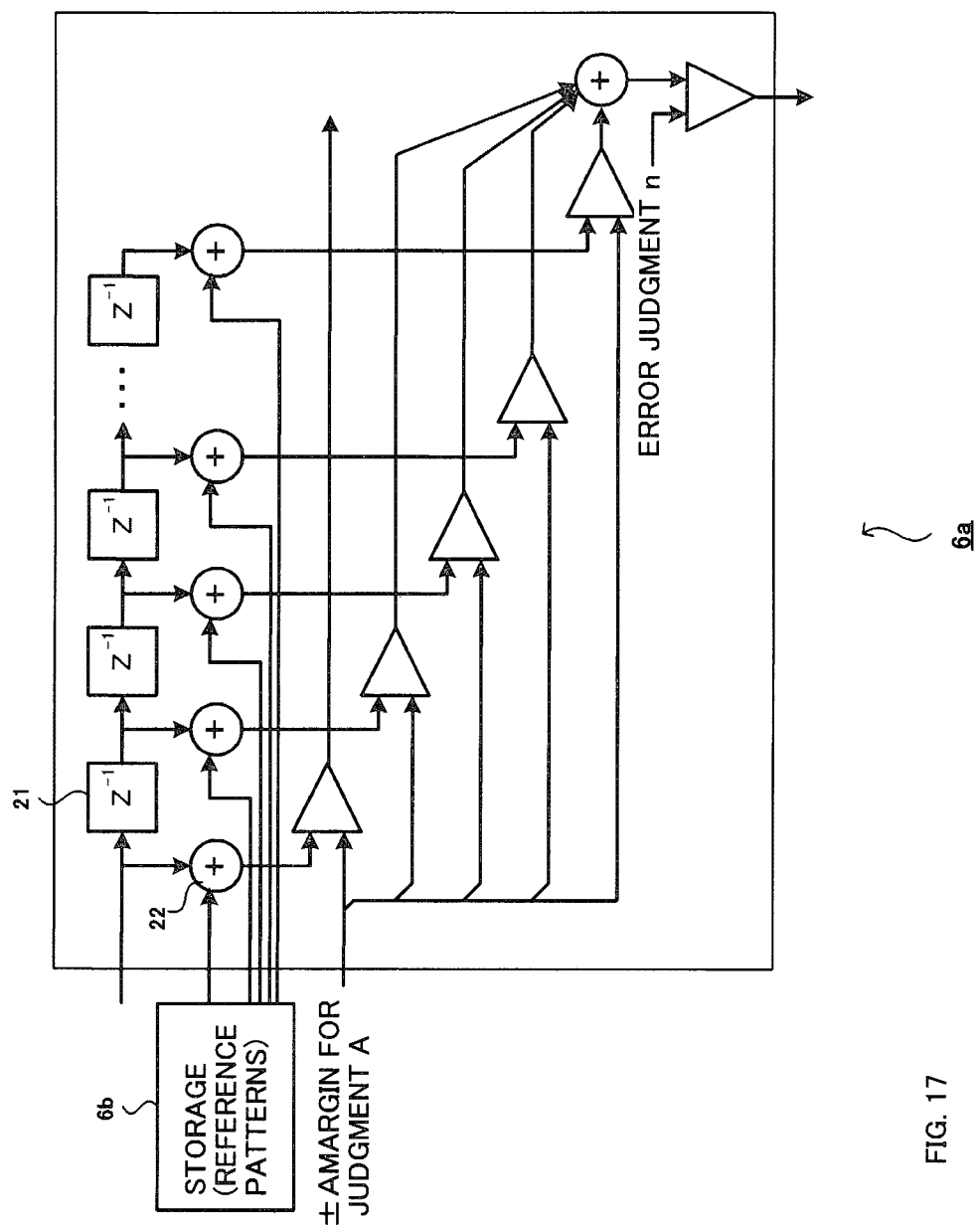
FIG. 17 illustrates another example of the circuit configuration of the heart rate error detecting unit.

In the circuit configuration as shown in FIG. 13, it is illustrated that the reference heart rate variation values E0 to En are set as existing values. However, as shown in FIG. 17, these reference heart rate variation values E0 to En may be set sequentially, from the storage 6b which stores the reference heart rate forming variation values. According to this configuration, just one circuit is needed to constitute the heart rate variation error detecting part 6a, unlike the case of FIG. 16 in which multiple circuits are connected.

Next, with reference to FIG. 18 to FIGS. 20A-D, the heart rate error correcting unit 6B will be explained.

Figure 18:
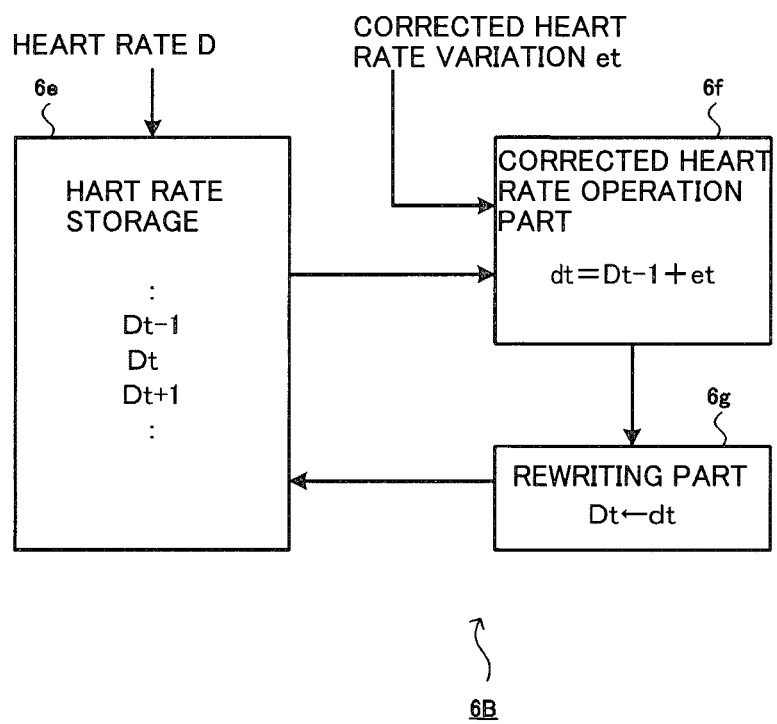
FIG. 18 illustrates an example of the circuit configuration constituting the heart rate error correcting unit.

FIG. 18 illustrates an example of the circuit configuration constituting the heart rate error correcting unit. In FIG. 18, the heart rate error correction unit 6B includes a heart rate storage 6e for storing the heart rate D, a corrected heart rate operation part 6f for obtaining a heart rate to be corrected, and a rewriting part 6e for rewriting the heart rate of the heart rate storage 6e by the corrected heart rate.

Figure 19:
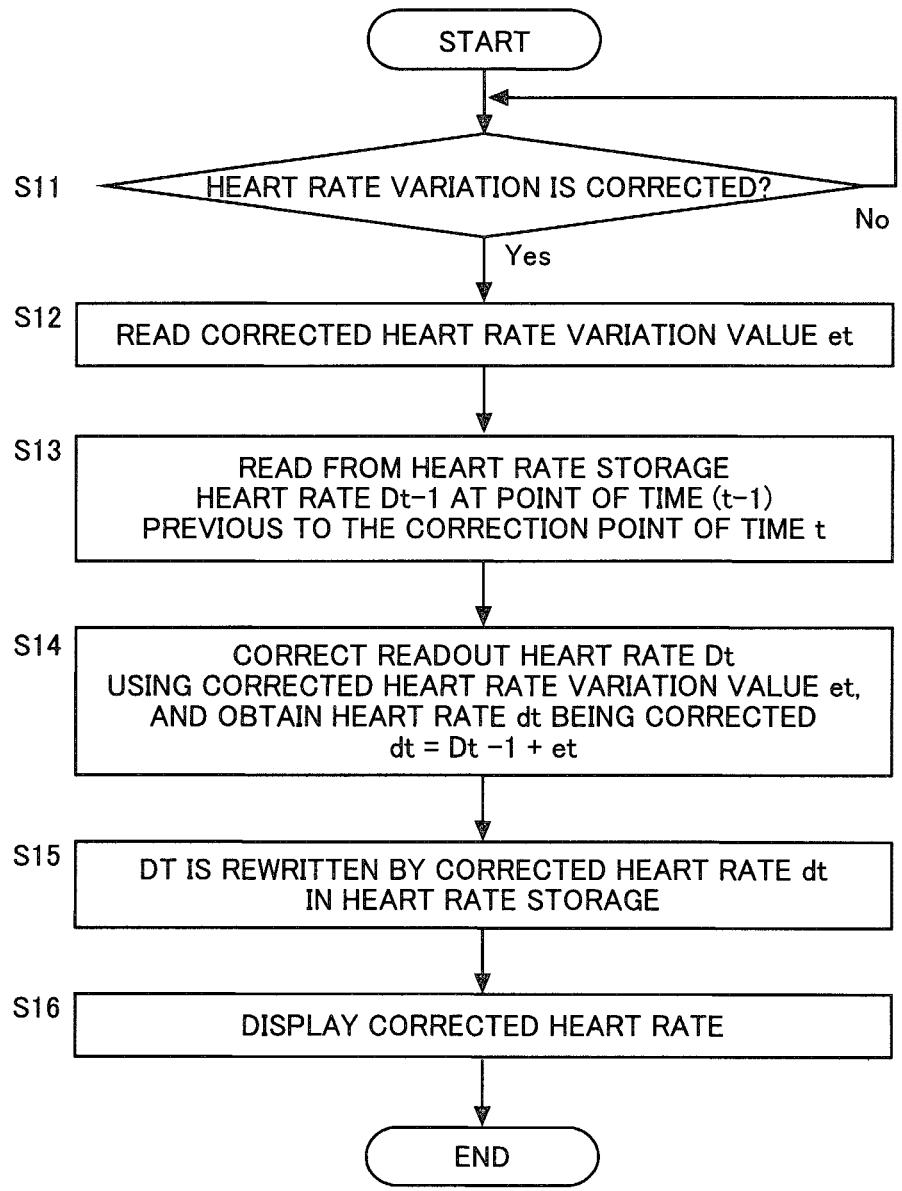
FIG. 19 shows a flowchart for explaining an operation example of the heart rate correcting unit.

Next, with reference to FIG. 19 showing the flowchart and FIGS. 20A-D showing the illustration for explaining the corrected heart rate, an operation example of the heart rate error correcting unit will be explained.

Figure 20A:
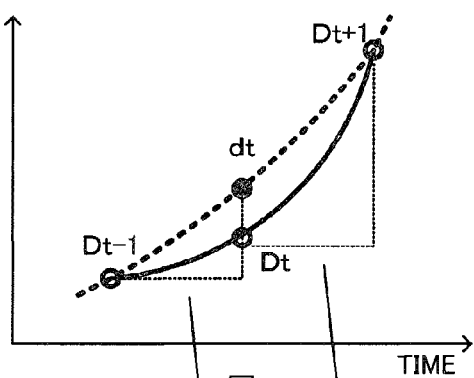
FIGS. 20A, B, C, and D show illustrations for explaining an operation example of the heart rate correcting unit.
Figure 20B:
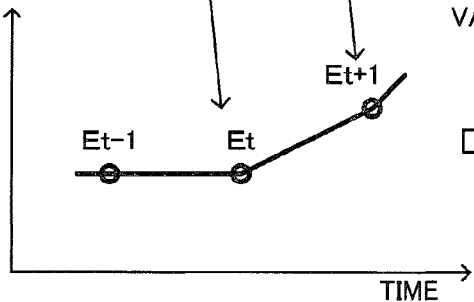
Figure 20D:
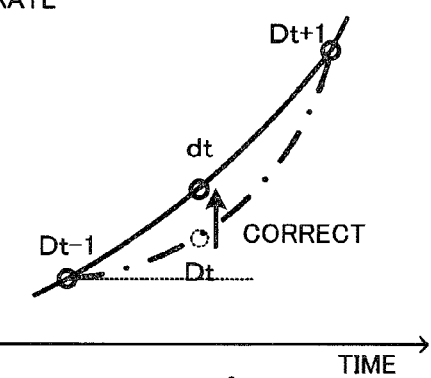
Figure 20C:
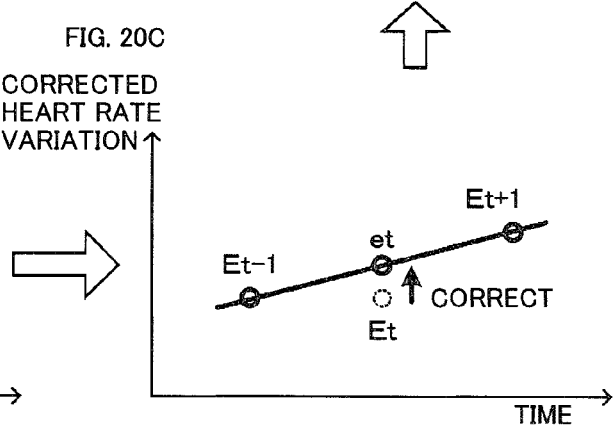

The heart rate variation value Et is represented by a difference between the heart rate Dt at the time of correction point of time t, and the heart rate Dt−1 at the point of time t−1 that is previous to the time t (FIG. 20A, FIG. 20B).

Here, if the heart rate variation is corrected from Et to et by the heart rate variation error correcting part 6d (FIG. 20C) (S11), the corrected heart rate operation part 6f reads the heart rate variation value et (corrected heart rate variation value E at the corrected point of time t), which is corrected by the heart rate variation error correcting part 6d as described above (S12), and reads the heart rate Dt−1 at the point of time t−1 previous to the same point of time t, from the heart rate storage 6e (S13).

The corrected heart rate operation part 6f uses the readout heart rate Dt−1 and the heart rate variation value et, and performs the operation;

$dt = Dt-1 + et$

Accordingly, a corrected heart rate dt is calculated (FIG. 20D) (S14).

The rewriting part 6g corrects the heart rate, by rewriting the heart rate Dt in the heart rate storage 6e by dt (S15).

The heart rate being corrected can be subjected to a display processing, including processing such as notification, transmission to other unit, or storing (S16).

Each processing described above may not be limited to a hardware configuration. Alternatively, each processing may be executed by the software processing according to programs that command the CPU to perform each of the processing.

Up to this point, an example has been shown in which the heart rate variation error detecting part 6a in the aforementioned heart rate error detecting unit 6A performs the detection of an error in the heart rate variation, according to the pattern of the successive heart rate variations (e.g., [E1, E2]). However, the error detection by using the heart rate variation is not limited to this configuration. For example, it is also possible to determine the detection of error only by the heart rate variation value E0 at a target point of time.

FIGS. 21A-C and FIG. 22 are illustrations and flowchart for explaining another aspect of the heart rate variation error detection according the present invention.

Figure 21A:
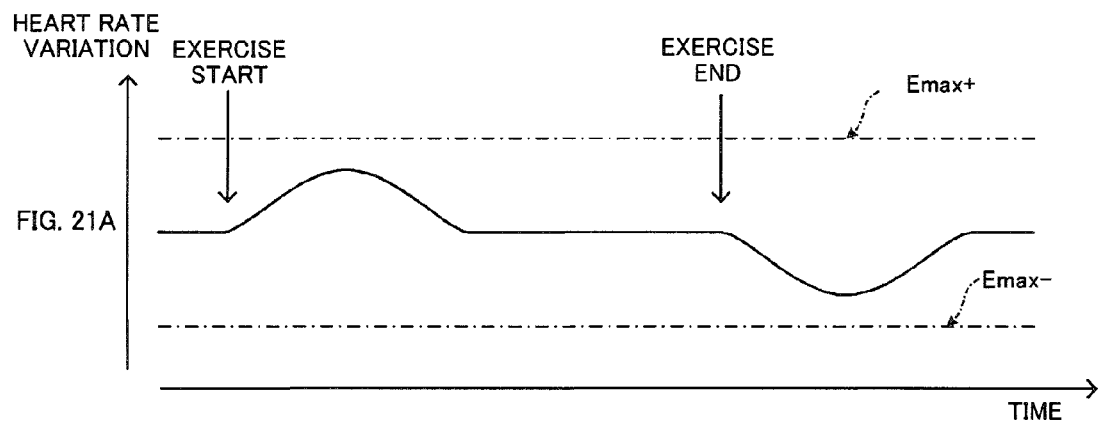
FIGS. 21A, B and C show illustrations for explaining another aspect for detecting a heart rate variation error according to the present invention.
Figure 21B:
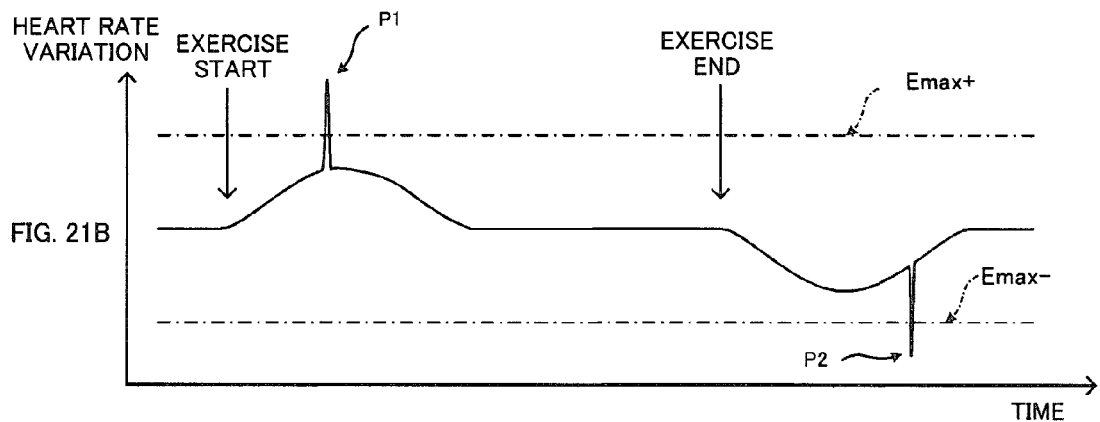

FIG. 21B illustrates a case where errors occurred in the heart rate variation at "P1" and "P2". For comparison, FIG. 21A shows a case where there occurs no error.

It is experimentally confirmed that the heart rate variation due to an exercise approximately fits into the range between the upper limit and the lower limit (e.g., ±20). Under this condition, the upper limit value Emax+ (e.g., +20) and the lower limit value Emax− (e.g., −20) are set in the heart rate variation, and it is determined that an error has occurred when the variation goes over this range. Accordingly, it is possible to perform simple error detection, even though the detecting precision is relatively deteriorated.

Figure 21C:
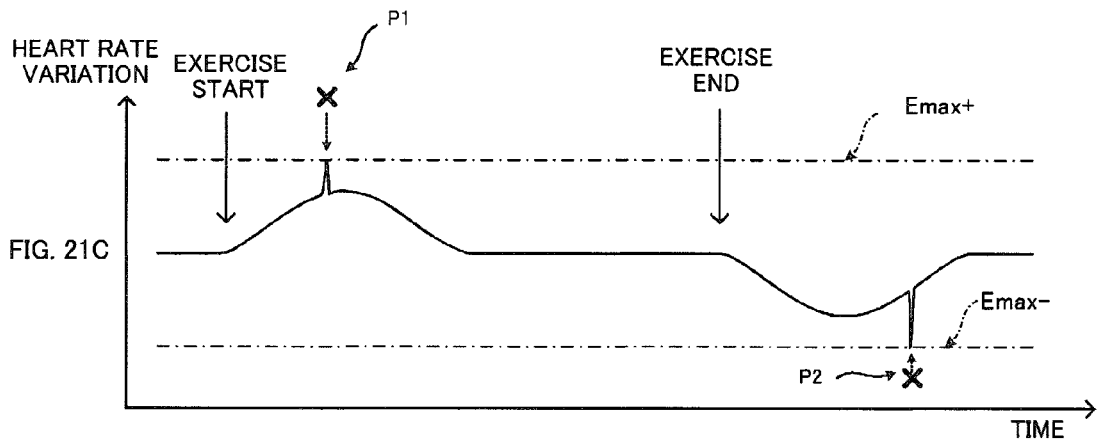

Moreover, if it is determined as an error when the variation goes over the upper limit or the lower limit, the error is simply corrected by setting the over value to the upper limit Emax+ or the lower limit Emax−. FIG. 21C illustrates an example that the value of "P1" that goes over the upper limit value Emax+ is corrected to be the value of Emax+, and the value of "P2" that goes over the lower limit value Emax− is corrected to be the value of Emax−.

Figure 22:
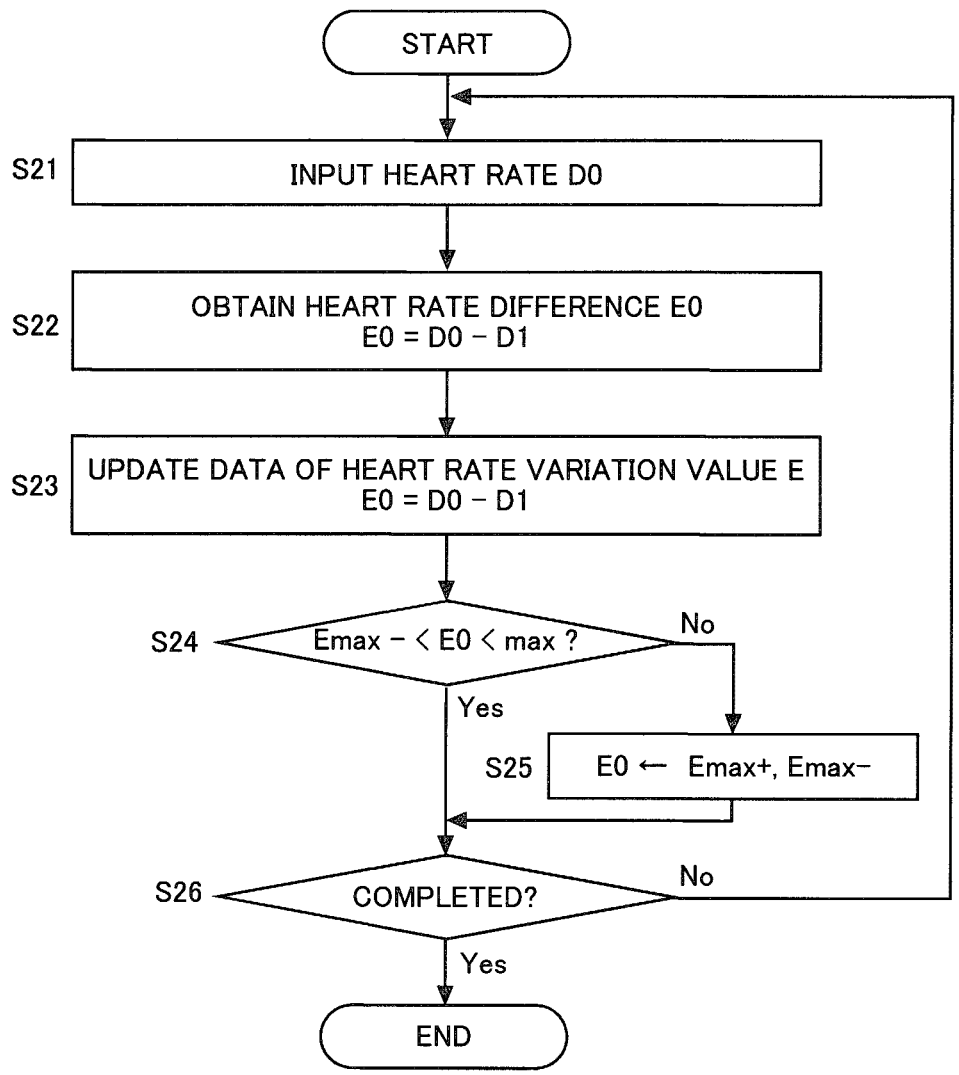
FIG. 22 shows a flowchart for explaining another aspect for detecting the heart rate variation error according to the present invention.

This processing for correcting the heart rate variation error can be performed according to the flowchart as shown in FIG. 22, for instance.

Firstly, a heart rate D is inputted from the heart rate detecting unit 4 into the heart rate temporary storage 5a, and it stores the heart rate D being inputted as the current heart rate D0, and simultaneously rewrites the current heart rate D0 previously stored as the previous heart rate D1 (S21).

The difference operation part 5b performs the operation (E0=D0−D1) for the difference between the current heart rate D0 and the previous heart rate D1 (S22).

The heart rate variation value obtained in the aforementioned operation is stored as the heart rate variation value E0 at the current point of time (S23).

Next, by using the upper limit value Emax+ and the lower limit Emax− of the heart rate variation, an error of the obtained heart rate variation value E0 is detected (S24).

When the heart rate variation value E0 is out of the range defined by the upper limit Emax+ and the lower limit Emax−, it is determined that there is an error in the heart rate variation value E0. When the heart rate variation value E0 goes over the upper limit value Emax+, the heart rate variation value E0 is set to be the upper limit value Emax+. When the heart rate variation value E0 goes over the lower limit value Emax−, the heart rate variation value E0 is set to be the lower limit value Emax− (S25).

It is to be noted here that in the comparison step of S24, if the heart rate variation value E0 falls into the rage defined by the upper limit value Emax+ and the lower limit value Emax−, it is determined that there is no error in the heart rate variation value as the evaluation target, and any correction is not needed. Every time when the heart rate variation is obtained, the steps S21 to S25 described above are repeated (S26).

With the error detection and the error correction performed in a simple manner as described above, it is not necessary to select a pattern for judgment, according to the exercise start or the exercise stop notified from the exercise notification unit.

INDUSTRIAL APPLICABILITY

A method for removing a noise in the heart beat waveform according to the present invention can be applied not only to a heart rate meter, but also to an apparatus that measures a body function using the heart rate as one data, such as a body function measuring apparatus.

What is claimed is:

1. A heart rate meter for measuring a heart rate of a living body, comprising:
a heart rate variation detecting unit for obtaining a heart rate variation determined from a heart beat waveform, and
a heart rate error detecting and correcting unit for detecting an error of the heart rate variation detecting unit based on a trend of the heart rate variation, and correcting the error of the heart rate variation detecting unit being detected.

2. The heart rate meter according to claim 1, wherein,
the heart rate variation detecting unit obtains a heart rate variation from a variation in the heart rate every predetermined period of time.

3. The heart rate meter according to claim 2, wherein,
the heart rate variation detecting unit obtains the heart rate variation from a difference in sampling values of the heart rate.

4. The heart rate meter according to claim 1, wherein,
the heart rate variation detecting unit obtains the heart rate variation from a differential value of the heart rate at a predetermined point of time.

5. The heart rate meter according to claim 1, wherein,
the heart rate variation is obtained from a heart beat waveform under a certain exercise load being applied.

6. The heart rate meter according to claim 1, wherein,
the heart rate error detecting and correcting unit comprises:
a heart rate error detecting unit for detecting the heart rate variation error based on the trend of the heart rate variation, so as to detect a heart rate error, and
a heart rate error correcting unit for correcting the error according to the heart rate error being detected.

7. The heart rate meter according to claim 6, wherein,
the heart rate error detecting unit further comprising,
a heart rate variation error detecting unit for comparing a trend of the heart rate variation of a target heart rate with a trend of a reference heart rate variation as a standard, and detecting an error in the target heart rate variation based on a trend similarity between both of the heart rate variations, and
a heart rate variation error correcting unit for correcting the heart rate variation error.

8. The heart rate meter according to claim 7, wherein,
the heart rate variation error detecting unit assumes;
multiple number of heart rate variation values included in the target heart rate variation within a predetermined time zone, as the trend of the heart rate variation,
the heart rate variation values of the same number held in the reference heart rate variation within the same predetermined time zone, as the trend of the reference heart rate variation, and
differences between the heart rate variation values associated respectively in both trends, as the trend similarity, and detects an error in the target heart rate variation.

9. The heart rate meter according to claim 7, further comprising,
a reference heart rate variation pattern storage, for storing multiple reference heart rate variation patterns, each being made up of a different combination of heart rate variation values, wherein,
the heart rate variation error detecting unit compares a reference heart rate variation pattern, estimated from the multiple reference heart rate variation patterns, with the target heart rate variation, and
assumes differences between the heart rate variation values associated respectively in both heart rate variations, as the trend similarity, so that an error in the target heart rate variation is detected.

10. The heart rate meter according to claim 9, wherein,
the heart rate variation error detecting unit reads the reference heart rate variation pattern from the reference heart rate variation pattern storage, in sync with timing when an exercise load is applied.

11. The heart rate meter according to claim 8, wherein,
the heart rate variation error detecting unit detects the heart rate variation error based on the number of the target heart rate variation values each having a difference which goes over a set value.

12. The heart rate meter according to claim 7, wherein,
the heart rate variation error correcting unit corrects the heart rate variation value of the target heart rate variation detected by the heart rate variation error detecting part to the heart rate variation value of the reference heart rate variation.

13. The heart rate meter according to claim 7, wherein,
the heart rate error correcting unit corrects an associating heart rate based on the heart rate variation value that is detected and corrected by the heart rate error detecting unit.

* * * * *